(12) United States Patent
Aicher et al.

(10) Patent No.: US 9,156,849 B2
(45) Date of Patent: Oct. 13, 2015

(54) APPLICATION OF β-FUNCTIONALIZED DIHYDROXY-CHLORINS FOR PDT

(75) Inventors: Daniel Aicher, Berlin (DE); Arno Wiehe, Berlin (DE); Christian B. W. Stark, Leipzig (DE); Volker Albrecht, Bergholz-Rehbrücke (DE); Susanna Gräfe, Jena (DE)

(73) Assignee: Biolitec Pharma Marketing LTD, Labuan (MY)

( * ) Notice: Subject to any disclaimer, the term of this patent is extended or adjusted under 35 U.S.C. 154(b) by 82 days.

(21) Appl. No.: 13/208,917

(22) Filed: Aug. 12, 2011

(65) Prior Publication Data

US 2013/0041307 A1    Feb. 14, 2013

(51) Int. Cl.
| | |
|---|---|
| *C07D 487/22* | (2006.01) |
| *A61K 38/00* | (2006.01) |
| *A61K 41/00* | (2006.01) |
| *A61K 49/00* | (2006.01) |

(52) U.S. Cl.
CPC .......... *C07D 487/22* (2013.01); *A61K 41/0071* (2013.01); *A61K 49/0036* (2013.01)

(58) Field of Classification Search
CPC .................................................. C07D 487/22
See application file for complete search history.

(56) References Cited

U.S. PATENT DOCUMENTS

2012/0263625 A1*  10/2012  Aicher et al. ................... 422/22

FOREIGN PATENT DOCUMENTS

WO    WO 2013015774    *  1/2013

OTHER PUBLICATIONS

Aicher et al. Synthesis of β-functionalized Temoporfin derivatives for an application in photodynamic therapy. 2011, Bioorganic & Medicinal Chemistry Letters, 21, 5808-11.*
Al-Omari, S.Photophysical properties and localization of chlorins substituted with methoxy groups, hydroxyl groups and alkyl chains in liposome-like cellular membrane. Biomedical Materials (Bristol, United Kingdom) (2007), 2(2), 107-115.*

* cited by examiner

*Primary Examiner* — Brian McDowell
(74) *Attorney, Agent, or Firm* — BJ Associates; Bolesh J. Skutnik

(57) ABSTRACT

The present invention provides biologically active compounds that can be used as photosensitizers for diagnostic and therapeutic applications, particularly for PDT of cancer, infections and other hyperproliferative diseases, fluorescence diagnosis and PdT treatment of a non-tumorous indication such as arthritis, inflammatory diseases, viral or bacterial infections, dermatological, ophthalmological or urological disorders. The compounds are of the class of β-functionalized hydroxy- and dihydroxy-chlorins having the general formula

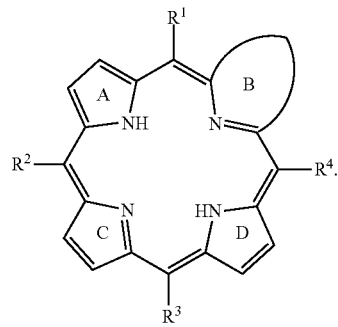

14 Claims, 7 Drawing Sheets

Wherein:

B is

1

2

3

4 n = 1,2,3,4,5,6,7 or 8

APPLICATION OF β-FUNCTIONALIZED DIHYDROXY-CHLORINS FOR PDT

BACKGROUND OF THE INVENTION

1. Field of the Invention

The invention relates to the chemistry of biologically active compounds. More particularly to β-functionalized chlorin derivatives that can be used as photosensitizers for a wide range of light irradiation treatments such as photodynamic therapy of cancer, infections and other diseases.

2. State of the Art

Photodynamic therapy (PDT) is one of the most promising new techniques now being explored for use in a variety of medical applications and particularly is a well-recognized treatment for the destruction of tumors. Photodynamic therapy uses light and a photosensitizer (a dye) to achieve its desired medical effect. A large number of naturally occurring and synthetic dyes have been evaluated as potential photosensitizers for photodynamic therapy. Perhaps the most widely studied class of photosensitizers are tetrapyrrolic macrocyclic compounds. Among them, especially porphyrins and chlorins have been tested for their PDT efficacy. Porphyrins are macrocyclic compounds with bridges of one carbon atom joining pyrroles to form a characteristic tetrapyrrole ring structure. There are many different classes of porphyrin derivatives including those containing dihydro-pyrrole units. Chlorins, as referred to in the present invention, are porphyrin derivatives, in which one double bond of the aromatic system in β-position is absent. As examples of tetrapyrrolic macrocyclic compounds used as photosensitizers, Patent Publication No US 04656186 by Bommer et al. discloses fluorescent mono, di- or polyamide of an aminocarboxylic acid and tetrapyrrole containing at least three carboxyl groups, U.S. Pat. No. 7,022,843B1 by MacAlpine et al. provides β,β'-dihydroxy meso-substituted chlorins as photosensitizers, and U.S. Pat. No. 7,166,719B2 by Pandey et al. discloses tetrapyrrole compounds containing a fluorinated substituent where the compound is a chlorin or a bacteriochlorin for PDT diagnostic and therapeutic application.

There are several properties that an effective photosensitizer should accomplish. Among them, a desirable characteristic in order to efficiently destroy deep target tissues is a strong absorption at long wavelength. Many current photosensitizers are not efficient enough as they have low absorption in the red region of the spectrum. Chlorins have the advantage that they possess an intense absorption in the red and near-infrared region of the electromagnetic spectrum. As light of longer wavelength penetrates deeper into the tissue, it is thus possible to treat e.g. more expanded tumors, if the PDT is employed for tumor therapy. Chlorins possessing potential for PDT can either be derived from natural sources or from total synthesis.

If the chlorins are derived from natural compounds they are usually obtained by derivatizing chlorophylls or bacteriochlorophylls, as for example the photosensitizers derived from chlorophyll a of photosynthetic plants and algae disclosed in U.S. Pat. No. 5,330,741 by Smith. Due to the sensibility of the natural compounds this is often difficult and requires vast resources. So, the synthesis of chlorins by total synthesis is an appealing alternative. Methods to prepare chlorins and bacteriochlorins by total synthesis are known in the art. Generally these compounds are prepared by first synthesizing the porphyrin and then converting the porphyrin system to a chlorin or bacteriochlorin system. This step can e.g. be performed by the reduction with in situ generated di-imine or by cis-dihydroxylation with osmium tetroxide (patent EP 00337601B1; patent application WO 09613504A1, patent application WO 00061584A1; C. Bruckner, D. Dolphin, 2,3-vic-Dihydroxy-meso-tetraphenylchlorins from the Osmium Tetroxide Oxidation of meso-Tetraphenylporphyrin, *Tetrahedron Lett.* 1995, 36, 3295-3298; C. Bruckner, D. Dolphin, β,β'-Dihydroxylation of meso-Tetraphenylchlorins, *Tetrahedron Lett.* 1995, 36, 9425-9428; F. Rancan, A. Wiehe, M. Nöbel, M. O, Senge, S. Al Omani, F. Böhm, M. John, B. Röder, Influence of substitutions on asymmetric dihydroxychlorins with regard to intracellular uptake, subcellular localization and photosensitization in Jurkat cells, *J. Photochem. Photobiol. B: Biology* 2005, 78, 17-28; I. Laville, T. Figueiredo, B. Loock, S. Pigaglio, Ph. Maillard, D. S. Grierson, D. Carrez, A. Croisy, J. Blais, Synthesis, Cellular Internalization and Photodynamic Activity of Glucoconjugated Derivatives of Tri and Tetra(meta-hydroxyphenyl)chlorines, *Bioorg. Med. Chem.* 2003, 11, 1643-1652).

Another class of chlorins possesses a diketo-group in one of the four pyrrolic subunits. However, these diketo-chlorins are not suitable for application in PDT e.g. due to their very weak absorption in the red region. Some different ways can be found in the art to synthesize these kinds of chlorins. A possible way is the direct oxidation of dihydroxychlorins obtained by dihydroxylation for example with 2,3-dichloro-5,6-dicyano-benzoquinone as oxidizing agent (H. W. Daniell, S. C. Williams, H. A. Jenkins, C. Brückner, Oxidation of meso-tetra-phenyl-2,3-dihydroxychlorin: simplified synthesis of β,β'-dioxochlorins, *Tetrahedron Lett.* 2003, 44, 4045-4049). An alternative method is the oxidation of 2-hydroxyporphyrins to the corresponding diketo-chlorins. This conversion can be accomplished by several oxidizing agents (R. Beavington, P. A. Rees, P. L. Burn; A study on the oxidation of 2-hydroxyporphyrins to porphyrin-α-diones, *J. Chem. Soc., Perkin Trans.* 1998, 1, 2847-2851). Interestingly, 2-hydroxyporphyrins show in solution tautomerism depending on the solvent and can exist in the keto or the enol form (M. J. Crossley, M. M. Harding, S. Sternhell, Tautomerism in 2-Hydroxy-5,10,15,20-tetraphenylporphyrin: An Equilibrium between Enol, Keto and Aromatic Hydroxyl Tautomers, *J. Org. Chem.* 1988, 53, 1132-1137). They can be synthesized either by dehydration of the corresponding dihydroxy-chlorins or by conversion of 2-nitroporphyrins (M. J. Crossley, L. G. King, S. M. Pyke, A new and highly efficient synthesis of hydroxyporphyrins, *Tetrahedron* 1987, 43, 4569-4577). A mild and selective method for β-nitration of porphyrins using $Cu(NO_3)_2$ in a mixture of acetic anhydride and acetic acid allows the nitration and metallation with copper in one step for a variety of porphyrins (A. Giraudeau, H. J. Callot, J. Jordan, I. Ezhar, M. Gross, Substituent effects in the electro reduction of porphyrins and metalloporphyrins, *J. Am. Chem. Soc.* 1979, 101, 3857-3862; J. P. C. Tomé, A. M. V. M. Pereira, C. M. A. Alonso, M. G. P. M. S, Neves, A. C. Tomé, A. M. S. Silva, J. A. S. Cavaleiro, M. V. Martínez-Diaz, T. Torres, G. M. A. Rahman, J. Ramey, D. M. Guldi, Synthesis and Photophysical Studies of New Porphyrin-Phthalocyanine Dyads with Hindered Rotation, *Eur. J. Org. Chem.* 2006, 257-267). Some further functionalizations of diketo-chlorins are known in the art, for example oxidative transformations (M. J. Crossley, L. G. King, Novel Heterocyclic Systems from Selective Oxidation at the β-Pyrrolic Position of Porphyrins, *Chem. Commun.* 1984, 920-922) or the synthesis of annulated heterocyclic systems (M. J. Crossley, P. L. Burn, S. J. Langford, S. M. Pyke, A. G. Stark, A New Method for the Synthesis of Porphyrin-α-diones that is Applicable to the Synthesis of Trans-annular extended Porphyrin Systems, *Chem. Commun.* 1991, 1567-1568). However, these compounds have no relevance with regard to an application in PDT. Thus, there is a need to have effective photosensitizers capable of efficiently destroying deep target tissues by intensively absorbing light in the red and near-infrared region of the electromagnetic spectrum.

OBJECTIVES AND BRIEF SUMMARY OF THE INVENTION

It is an aim of the present invention to provide biologically active compounds that can be used as photosensitizers for a wide range of applications including light irradiation treatments such as photodynamic therapy of cancer, infections and other diseases.

It is an objective of the present invention to use the chemically stable chlorin derivatives for various medical applications such as photodynamic therapy.

It is yet an objective of the present invention to provide β-functionalized hydroxy- and dihydroxy-chlorin structures that can be used in the photodynamic therapy of tumors and other hyperproliferative diseases, dermatological disorders, viral or bacterial infections, ophthalmological disorders or urological disorders.

It is a further objective of the present invention to provide β-functionalized hydroxy- and dihydroxy-chlorin structures that can be used for the fluorescence diagnosis and PDT treatment of a non-tumorous indication such as arthritis and similar inflammatory diseases.

It is another objective of the present invention to provide a method to prepare diketo-chlorins as precursors.

It is yet another objective of the present invention to provide a method to convert the diketo-chlorin precursors to β-functionalized hydroxy- and dihydroxy-chlorins.

It is yet a further objective of the present invention to provide highly amphiphilic compounds to be used in the PDT-treatment of tumors, dermatological disorders, viral or bacterial infections, ophthalmological disorders or urological disorders.

It is still another objective to provide pharmaceutically acceptable formulations for the biologically active compounds of the present invention such as a liposomal formulation to be injected avoiding undesirable effects like precipitation at the injection site or delayed pharmacokinetics of the tetrapyrrole systems.

Briefly stated, the present invention provides methods to obtain biologically active compounds that can be used as photosensitizers for diagnostic and therapeutic applications, particularly for PDT of cancer, infections and other hyperproliferative diseases, fluorescence diagnosis and PDT treatment of a non-tumorous indication such as arthritis, inflammatory diseases, viral or bacterial infections, dermatological, ophthalmological or urological disorders. An embodiment of the present invention consists of a method to synthesize diketo-chlorins as precursors. In yet another embodiment these precursors are converted to β-functionalized hydroxy- and dihydroxy-chlorins. Another embodiment is to provide amphiphilic compounds with a higher membrane affinity and increased PDT-efficacy. Another embodiment of the present invention consists of formulating the desired isomer into a liposomal formulation to be injected avoiding undesirable effects like precipitation at the injection site or delayed pharmacokinetics of the tetrapyrrole systems.

The above and other objects, features and advantages of the present invention will become apparent from the following description read in conjunction with the accompanying drawings.

DETAILED DESCRIPTION OF PREFERRED EMBODIMENTS

The present invention provides biologically active compounds that can be used as photosensitizers for a wide range of light irradiation treatments such as photodynamic therapy of cancer, hyperproliferative diseases, dermatological disorders, viral or bacterial infectious diseases, ophthalmological disorders and/or urological disorders. The alternative photosensitizers provided by the present invention have the advantage that they are easily produced and characterized. The present invention allows the further functionalization of effective photosensitizers to enhance their activity, stability or make new applications possible. Moreover, as the present invention provides methods to tailor amphiphilic compounds for desired PDT applications, target tissue selectivity is increased and thus PDT efficacy. The present invention enhances the effectiveness of prior art biologically active compounds offering a deeper tissue penetration due to their strong absorption at long wavelength of the red and near-infrared region of the electromagnetic spectrum, enhanced selectivity for target tissues over healthy surrounding tissues due to its tailored amphiphilicity and custom-made pharmacokinetic behavior depending on the particular PDT application.

The biologically active compounds of the present invention that can be used for different medical indications, particularly PDT, are meso-substituted and β-functionalized hydroxy- or dihydroxy-chlorin structures. Additionally, the invention extends their applications as the structures can be employed for fluorescence diagnosis and PDT treatment of non-tumorous indications such as arthritis and similar inflammatory diseases.

Figure 1:
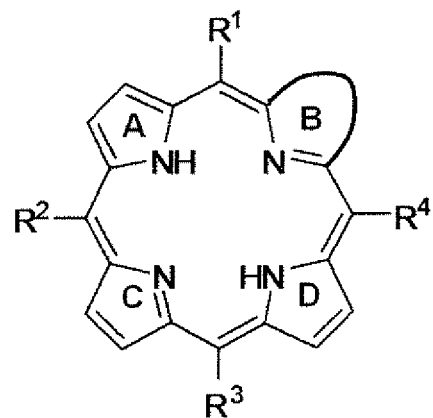
FIG. 1—depicts the general formula of an embodiment of a tetrapyrrolic compound of present invention.
Figure 1:
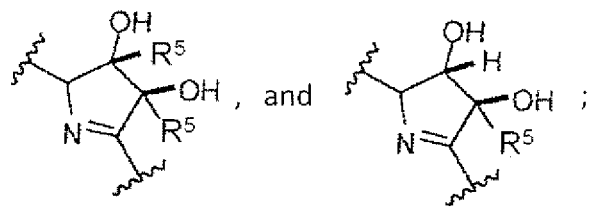

In a preferred embodiment, a tetrapyrrolic compound has the general formula as depicted in FIG. 1. Wherein B is as stated in FIG. 1 and $R^1$, $R^2$, $R^3$ and $R^4$ are independently hydrogen, a substituted or unsubstituted alkyl or fluoroalkyl group consisting of 1-15 carbon atoms, or a substituted or unsubstituted aromatic ring; $R^5$ is a substituted or unsubstituted alkyl, alkenyl, alkinyl or fluoroalkyl group consisting of 1-15 carbon atoms, or a substituted or unsubstituted aromatic ring. Some more specific examples are presented below as well as in FIGS. 2-8.

Figure 2:
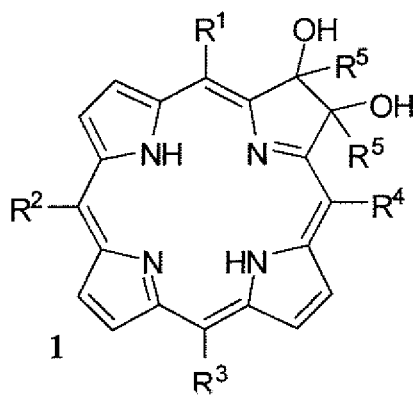
FIG. 2—shows the general formulas 1 and 2, which are the basis for some embodiments of tetrapyrrolic compounds of present invention.
Figure 2:
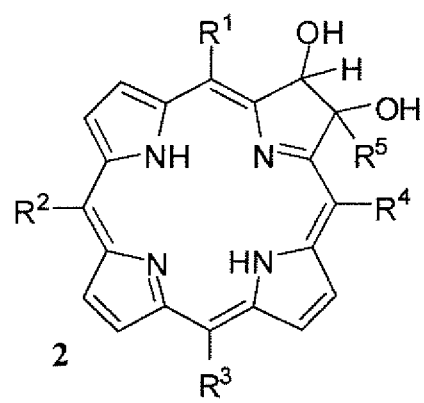

In another embodiment, a tetrapyrrolic compound is based on the formulas 1 or 2 depicted in FIG. 2, wherein $R^1$, $R^2$, $R^3$ or $R^4$ are independently a hydrogen, a substituted or unsubstituted alkyl, or fluoroalkyl group consisting of 1-15 carbon atoms, a substituted or unsubstituted aromatic ring; and $R^5$ is a substituted or unsubstituted alkyl, alkenyl, alkinyl or fluoroalkyl group consisting of 1-15 carbon atoms or a substituted or unsubstituted aromatic ring.

In another embodiment, a tetrapyrrolic compound is based on the formulas 1 or 2 depicted in FIG. 2; and $R^1$, $R^2$, $R^3$ or $R^4$ are independently a hydrogen, a substituted or unsubstituted alkyl, or a fluoroalkyl group consisting of 1-15 carbon atoms, a phenyl ring or a phenyl ring with one or more substituents X either in the ortho-, meta- or para-position. Substituent X is preferably OH, —COOH, —$NH_2$, —$CF_3$, —F, —COOY, —NHY, —OY, —NH—Z—COOH, or —CO—Z—$NH_2$; substituent Y is a polyethylene glycol residue containing a $(CH_2CH_2O)_n$ moiety with n=1-30; and substituent in Z are peptides or oligopeptides. $R^5$ is a substituted or unsubstituted alkyl, alkenyl, alkinyl or fluoroalkyl group consisting of 1-15 carbon atoms, a phenyl ring or a phenyl ring with one or more substituents X either in the ortho-, meta- or para-position. For $R^5$, the substituent X is OH, —COOH, —$NH_2$, —$CF_3$, —F, —COOY, —NHY, —OY, —NH—Z—COOH, or —CO—Z—$NH_2$; the substituent Y is a polyethylene glycol residue containing a $(CH_2CH_2O)_n$ moiety with n=1-30 or a carbohydrate moiety; and the substituent Z are peptides or oligopeptides.

In another embodiment, a tetrapyrrolic compound is based on the formulas 1 or 2, as described in FIG. 2, wherein $R^1$, $R^2$, $R^3$ and $R^4$ are independently hydrogen, a substituted or unsubstituted alkyl, or fluoroalkyl group consisting of 1-15 carbon atoms, a phenyl ring or a phenyl ring with one or more substituents X either in the ortho-, meta- or para-position; substituent X is OH, —COOH, —$NH_2$, —$CF_3$, —F, —COOY, —NHY, —OY, —NH—Z—COOH, or —CO—Z—$NH_2$; substituent Y is a polyethylene glycol residue containing a $(CH_2CH_2O)_n$ moiety with n=1-30: and substituent Z are peptides or oligopeptides. $R^5$ is a substituted or unsubstituted alkyl, alkenyl, alkinyl or fluoroalkyl group consisting of 1-15 carbon atoms or a phenyl ring substituted with one or more $CF_3$-groups either in the ortho-, meta- or para-position.

In another embodiment, a tetrapyrrolic compound is based on the formulas 1 or 2, depicted in FIG. 2, wherein $R^1$, $R^2$, $R^3$ or $R^4$ are independently a substituted or unsubstituted alkyl or fluoroalkyl group consisting of 4-15 carbon atoms or a phenyl ring with one or more substituents X either in the meta- or para-position, and substituent X is OH, —COOH, —$NH_2$. In this formula $R^5$ is a substituted or unsubstituted alkyl, alkenyl or fluoroalkyl group consisting of 1-15 carbon atoms or a phenyl ring substituted with one or more $CF_3$-groups either in the ortho-, meta- or para-position.

Figure 3:
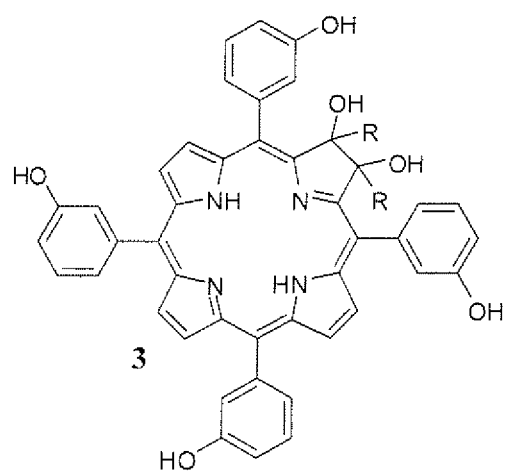
FIG. 3—shows another embodiment wherein the tetrapyrrolic compounds of present invention are based on the formula 3.

In another embodiment, a tetrapyrrolic compound is based on the formula 3, depicted in FIG. 3, wherein R is a substituted or unsubstituted alkyl, alkenyl, alkinyl or fluoroalkyl group consisting of 1-15 carbon atoms, a phenyl ring or a phenyl ring with one or more substituents X either in the ortho-, meta- or para-position; substituent X is OH, —COOH, —$NH_2$, —$CF_3$, —F, —COOY, —NHY, —OY, —NH—Z—COOH, or —CO—Z—$NH_2$; substituent Y is a polyethylene glycol residue containing a $(CH_2CH_2O)_n$ moiety with n=1-30 or a carbohydrate moiety; and substituent Z are peptides or oligopeptides.

In another embodiment, a tetrapyrrolic compound is based on the formula 3, as depicted in FIG. 3, wherein R is a substituted or unsubstituted alkyl, alkenyl, alkinyl or fluoroalkyl group consisting of 1-15 carbon atoms or a phenyl ring substituted with one or more $CF_3$-groups either in the ortho-, meta- or para-position.

Figure 4:
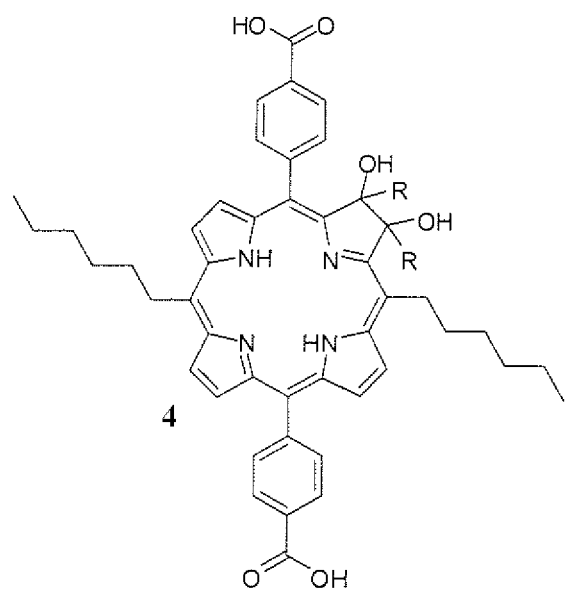
FIG. 4—shows another embodiment wherein tetrapyrrolic compounds are based on the formula 4.

In another embodiment, a tetrapyrrolic compound is based on the formula 4, depicted in FIG. 4, wherein R is a substituted or unsubstituted alkyl, alkenyl, alkinyl or fluoroalkyl group consisting of 1-15 carbon atoms, a phenyl ring or a phenyl ring with one or more substituents X either in the ortho-, meta- or para-position; substituent X is OH, —COOH, —$NH_2$, —$CF_3$, —F, —COOY, —NHY, —OY, —NH—Z—COOH, or —CO—Z—$NH_2$; substituent Y is a polyethylene glycol residue containing a $(CH_2CH_2O)_n$ moiety with n 1-30 or a carbohydrate moiety; and substituent Z are peptides or oligopeptides.

In another embodiment, a tetrapyrrolic compound is based on the formula 4, as described in FIG. 4, wherein R is a substituted or unsubstituted alkyl, alkenyl, alkinyl or fluoroalkyl group consisting of 1-15 carbon atoms or a phenyl ring substituted with one or more $CF_3$-groups either in the ortho-, meta- or para-position.

In another embodiment, a tetrapyrrolic compound is based on the formula 5, wherein R is a substituted or unsubstituted alkyl, alkenyl, alkinyl or fluoroalkyl group consisting of 1-15 carbon atoms, a phenyl ring or a phenyl ring with one or more substituents X either in the ortho-, meta- or para-position; substituent X is OH, —COOH, —$CF_3$, —F, —COOY, —NHY, —OY, —NH—Z—COOH, or —CO—Z—$NH_2$; substituent Y is a polyethylene glycol residue containing a $(CH_2CH_2O)_n$ moiety with n=1-30 or a carbohydrate moiety; and substituent Z are peptides or oligopeptides.

Figure 5:
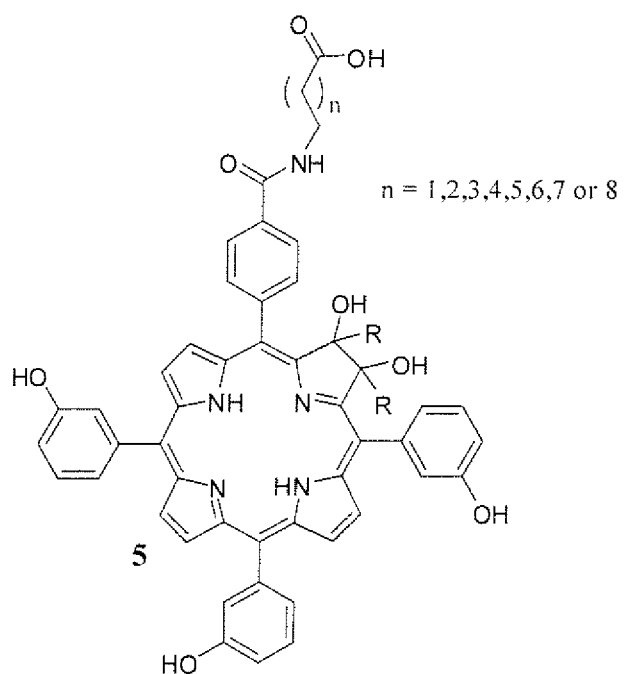
FIG. 5—shows another embodiment wherein tetrapyrrolic compounds are based on the formula 5.

In another embodiment, a tetrapyrrolic compound is based on the formula 5, as depicted in FIG. 5, wherein R is a substituted or unsubstituted alkyl, alkenyl, alkinyl or fluoroalkyl group consisting of 1-15 carbon atoms or a phenyl ring substituted with one or more $CF_3$-groups either in the only-, meta- or para-position.

Figure 6:
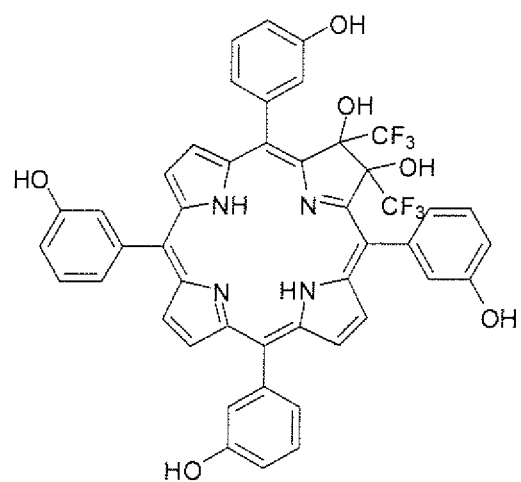
FIG. 6—shows another embodiment wherein a tetrapyrrolic compound is based on the formula 3.
Figure 7:
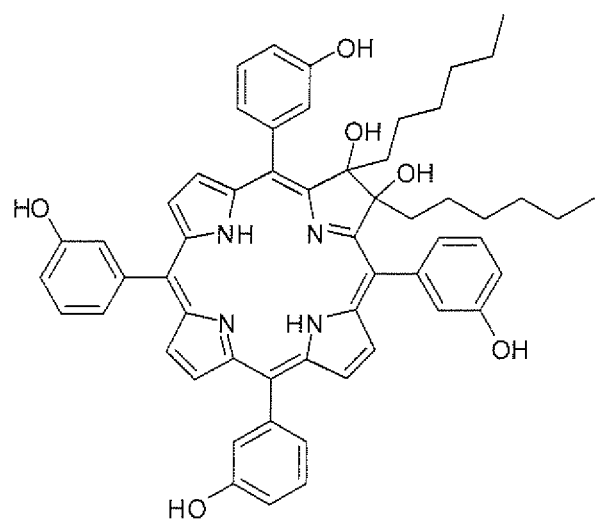
FIG. 7—shows another embodiment of a tetrapyrrolic compound of present invention based on formula 3.
Figure 8:
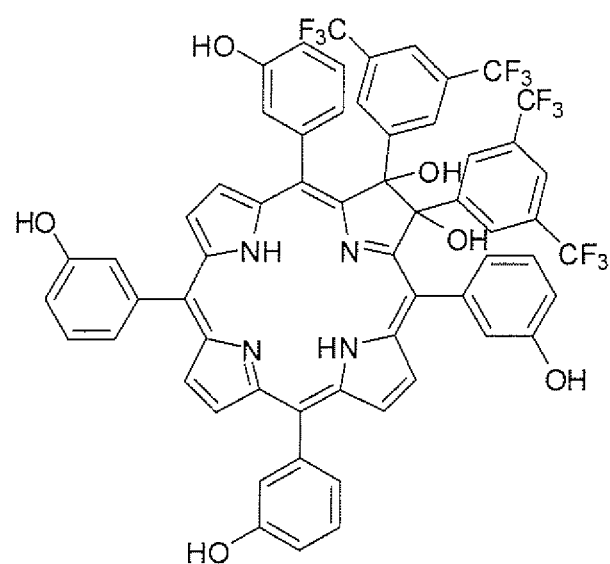
FIG. 8—shows another embodiment of a tetrapyrrolic compound of present invention based on formula 3.

In another embodiment as depicted in FIG. 6, a tetrapyrrolic compound is based on the formula 3, wherein R is a —$CF_3$ or a pharmaceutically acceptable derivative thereof. In yet another embodiment shown in FIG. 7, a tetrapyrrolic compound is based on the formula 3, wherein R is a hexane or a pharmaceutically acceptable derivative thereof. In another embodiment shown in FIG. 8, a tetrapyrrolic compound is based on the formula 3 or a pharmaceutically acceptable derivative thereof.

In another embodiment, the tetrapyrrolic compounds of all previous embodiments based on formulas 1, 2, 3, 4 and 5, or a pharmaceutically acceptable derivative thereof, are used for the preparation of pharmaceutical compositions for diagnosis and photodynamic therapy.

In another embodiment, a pharmaceutical composition comprises a tetrapyrrolic compound according to previous embodiments, or a pharmaceutically acceptable derivative thereof as an active ingredient.

In another embodiment, the pharmaceutical composition in which any of the tetrapyrrolic compounds of previous embodiments is an active ingredient is a liposomal formulation.

In another embodiment, a pharmaceutical composition in which a tetrapyrrolic compound according to all previous embodiments, or a pharmaceutically acceptable derivative thereof, is conjugated to a targeting agent. Preferably, the targeting agent of the pharmaceutical composition is an antibody, a fragment of an antibody, a peptide. This pharmaceutical composition is preferably a liposomal formulation.

In another embodiment, the tetrapyrrolic compounds of all previous embodiments based on formulas 1, 2, 3, 4 and 5, or a pharmaceutically acceptable derivative thereof, are used in photodynamic therapy of tumors, dermatological disorders, viral or bacterial infections, ophthalmological disorders or urological disorders, arthritis and similar inflammatory diseases. Additionally, the mentioned compounds or pharmaceutically acceptable derivative thereof can be used in the diagnosis of arthritis and similar inflammatory diseases.

In another embodiment, the tetrapyrrolic compounds depicted in previous embodiments are used in different therapeutic formulations according to the way of administration, comprising known carriers such as conventional liposomes, pegylated liposomes, nanoemulsions, nanocrystrals, nanoparticles, fatty emulsions, lipidic formulations, self-microemulsifying-drug-delivery-systems, Alpha-Feto protein (AFP), Bovine-Serum-Albumin (BSA), poly(lactic-co-glycolic acid) (PLGA), fatty emulsions and organic or non-organic nanoparticles.

In order to obtain the novel photosensitizers the present invention uses chemically stable porphyrin derivatives and provides methods for preparation of the corresponding precursor diketo-chlorins.

An embodiment of the present invention consists of a method to synthesize hydroxy- or dihydroxy-chlorins from diketo-chlorins as precursors using nucleophilic agents like (trifluoromethyl)trimethylsilane or Grignard reagents e.g. methylmagnesium bromide, hexylmagnesium bromide, 3,5-(bistrifluoromethyl)phenylmagnesium bromide or allylmagnesium chloride.

Another embodiment of the present invention consists of the steps of synthesizing a porphyrin with a defined arrangement of substituents, converting it to the diketo-chlorin and after that to the corresponding hydroxy- or dihydroxy-chlorins and then to formulate the desired compound into a liposomal formulation.

In yet another embodiment of the present invention an $A_4$-type porphyrin with m-methoxyphenyl substituents is synthesized and converted to the precursor diketo-chlorin which is converted to the corresponding β-functionalized dihydroxy-chlorin. Then, the remaining methoxy groups are deprotected with $BBr_3$ to obtain the hydroxyl substituted derivative.

In yet another specifically preferred embodiment of the present invention a porphyrin of the 'trans'-$A_2B_2$-type is synthesized, having hexyl chains as substituent A and methoxycarbonyl phenyl residues as substituent B. This porphyrin is converted to the dihydroxychlorin and after that to the diketo-chlorin. Then, the precursor is converted to the β-functionalized dihydroxy-chlorin and the remaining methyl esters are hydrolyzed to receive the corresponding carboxylic acids.

Acceptable starting materials for the synthesis of the porphyrins which are the subject of the present invention are pyrrole and aldehydes. They are subjected to a condensation reaction. Suitable methods for this condensation have long been known in the art (J. S. Lindsey, I. C. Schreiman, H. C. Hsu, P. C. Kearney and A. M. Marguerettaz, *J. Org. Chem.* 1987, 52, 827-836). Alternatively, the unsymmetrically substituted porphyrins can also be synthesized using dipyrromethanes and aldehydes, as is also known in the art (C.-H. Lee, J. S. Lindsey, One-Flask Synthesis of Meso-Substituted Dipyrromethanes and Their Application in the Synthesis of Trans-Substituted Porphyrin Building Blocks, *Tetrahedron* 1994, 50, 11427-11440). After condensation and purification of the desired porphyrins these are converted to the diketo-chlorins by two different methods.

The first method is exemplified with examples 1.1, 1.3 and 1.5 and proceeds over 3 steps. The first step is an osmium tetroxide mediated dihydroxylation as it is known in the art. The second step is the quantitative dehydration of the diol to form the corresponding 2-hydroxyporphyrin in refluxing trifluoroacetic acid. Thus, another embodiment of the present invention provides a simple method for the dehydration of the dihydroxychlorins. The Dess-Martin periodinane mediated oxidation of the 2-hydroxyporphyrin to the diketo-chlorin is the last step of the synthesis.

The second method is also known in the art and exemplified with examples 1.2 and 1.4. It is an alternative route to obtain 2-hydroxyporphyrins avoiding the use of osmium tetroxide. In the first step the porphyrin is converted to the corresponding Cu (II) nitro-porphyrin derivative using $Cu(NO_3)_2$ and in the second step the 2-hydroxyporphyrin is obtained by treating the nitro substituted porphyrin derivative with the sodium salt of E-benzaldehyde oxime in dimethyl sulfoxide in the presence of sodium hydride.

The β-functionalization of the diketo-chlorins is exemplified with examples 2 and 3. Example 2 shows the synthesis of trifluoromethyl substituted hydroxy- and dihydroxy-chlorins using (trifluoromethyl)trimethylsilane as nucleophilic agent. Example 3 shows the synthesis of alkyl, alkenyl, alkynyl and aryl substituted hydroxy- and dihydroxy-chlorins using organometallic, more precisely Grignard reagents.

The specifically substituted amphiphilic chlorin derivatives produced according to the present invention are suitable to be used for photodynamic therapy of cancer and other (hyper) proliferative diseases and infections.

PDT is accomplished by first incorporating the derivatives into a pharmaceutically acceptable application vehicle (e.g. ethanolic solution or liposomal formulation) for delivery of the derivatives to a specific treatment site. After administering the derivatives in the vehicle to a treatment area, sufficient time is allowed so that the chlorin derivatives preferentially accumulate in the diseased tissue. Lastly, the treatment area is irradiated with light of a proper wavelength and sufficient power to activate the porphyrin derivatives to induce necrosis or apoptosis in the cells of said diseased tissue. Thus, one of the main advantages is that convenient pharmaceutical formulations can be created for the biologically active compounds of the present invention such as liposomal formulation to be injected avoiding undesirable effects like precipitation at the injection site or delayed pharmacokinetics of the tetrapyrrole systems. Due to their amphiphilic nature, the chemically stable chlorin derivatives of the present invention can be prepared in various pharmaceutically acceptable and active preparations for different administration methods, e.g. injections. In a specifically preferred embodiment such amphiphilic compounds are formulated into liposomes. This liposomal formulation can then be injected avoiding undesirable effects such as precipitation at the injection site or delayed pharmacokinetics of the tetrapyrrole systems.

Determination of dark toxicity (DT) and phototoxicity (examples 5.1, 5.2 and 5.3) of three specific chlorin derivative of the present invention in cell culture experiments with a HT 29 cell line showed the excellent properties of the compounds for use in PDT.

As another object of the present invention is to use the disclosed porphyrin and chlorin derivatives in the diagnosis and treatment of arthritis and similar inflammatory diseases, the data presented in examples 6.1, 6.2 and 6.3 show the remarkable results of the photodynamic treatment of two cell lines especially relevant for arthritis (HIG82 and J774A.1, a rabbit synoviocyte and a mouse macrophage cell line) with three compounds of the present invention.

The following examples are presented to provide those of ordinary skill in the art with a full and illustrative disclosure and description of how to make the chlorin derivatives of the invention and show their photodynamic activity and are not intended to limit the scope of what the inventor regards as the invention. Efforts have been made to ensure accuracy with respect to numbers used (e.g. amounts, temperature etc.), but some experimental errors and deviations should be accounted for. Also, best measures have been taken to name the compounds with their systematic IUPAC name, nevertheless the basic reference are the given structural formulas based on the experimental spectroscopic data.

EXAMPLES

All reagents were used as purchased from commercial suppliers. Tetrahexylporphyrin, tetraphenylporphyrin and tetrakis-(3-methoxyphenyl)-porphyrin were prepared using Lindsey's conditions (J. S. Lindsey, I. C. Schreiman, H. C. Hsu, P. C. Kearney and A. M. Marguerettaz, *J. Org. Chem.* 1987, 52, 827-836). Dichloromethane was purified by distillation over $K_2CO_3$ prior to use. Thin layer chromatography (TLC) was performed using Merck silica gel 60 (without fluorescence indicator) pre-coated on aluminum sheets. Flash chromatography was carried out using Fluka silica gel 60, 0.040-0.063 mm (230-400 mesh). $^1H$ and $^{13}C$ NMR spectra were recorded in $CDCl_3$, $(CD_3)_2CO$, $CD_3OD$ or $(CD_3)_2SO$ on Bruker AC 250, AC 500, ECX 400 or AMX 500 instruments. Chemical shifts δ are given in ppm relative to TMS as internal standard or relative to the resonance of the residual solvent peak, J values are given in Hz. Mass spectra were recorded on Varian MAT 771, Varian IonSpec QFT-7 or Agilent 6210 ESI-TOF instruments. Electronic absorption spectra were recorded on a Specord S300 (Analytik Jena) spectrophotometer using dichloromethane or acetone as solvent.

Example 1

Preparation of Diketo-Chlorins 1.1 Preparation of
5,10,15,20-tetrahexyl-7,8-dioxo-7,8-chlorin 1.1.1 Preparation of
5,10,15,20-tetrahexyl-7,8-dihydroxy-7,8-chlorin In a typical experiment, osmium tetroxide (1 g, 3.9 mmol) was added to a stirred solution of 5,10,15,20-tetrahexylporphyrin (2.5 g, 3.9 mmol) in dichloromethane/pyridine 1:1 (195 ml). After stirring for 6 h, a saturated solution of sodium bisulfite in water/methanol 1:1 (100 ml) was added and the mixture was stirred for 18 h. The reaction mixture was filtered through Celite and dried over anhydrous sodium sulfate. The solvent was evaporated and the residue was purified by flash chromatography with dichloromethane/ethyl acetate 95:5 as eluent, followed by recrystallization from dichloromethane/aqueous methanol. The first band from the column contained starting material (591 mg, 24%) and the second band the title compound 5,10,15,20-tetrahexyl-7,8-dihydroxy-7,8-chlorin (1709 mg, 65%).

5,10,15,20-Tetrahexyl-7,8-dihydroxy-7,8-chlorin

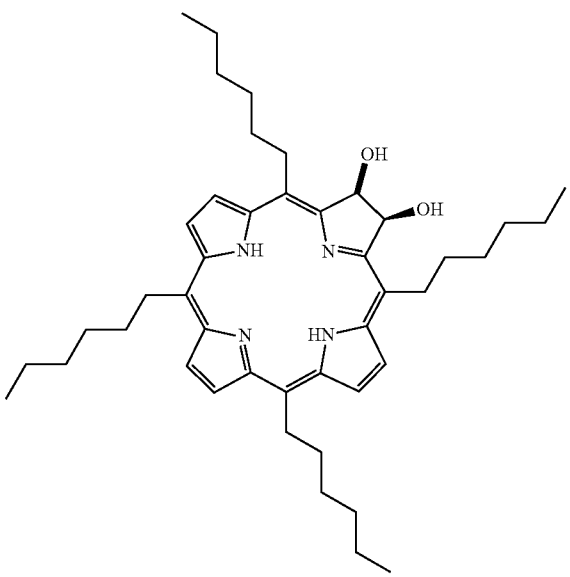 [SMILES: CCCCCCc1c2nc(c(CCCCCC)c3ccc([nH]3)c(CCCCCC)c3nc(c(CCCCCC)c4ccc1[nH]4)[C@@H](O)[C@H]3O)C=C2]

violet solid; mp: 109° C.; $\lambda_{max}(CH_2Cl_2)$/nm 409 (ε/dm$^3$ mol$^{-1}$ cm$^{-1}$ 219300), 431 (163500), 532 (21200), 559 (28500), 597 (12800) and 651 (22000); $\delta_H$ (500 MHz; CDCl$_3$) 9.03 (s, 2H, β-H), 8.67 (d, J=4.7 Hz, 2H, β-H), 8.48 (d, J=4.7 Hz, 2H, β-H), 5.72 (s, 2H, β-H), 4.30-4.37 (m, 2H, CH$_2$), 4.14-4.20 (m, 2H, CH$_2$), 3.73-3.86 (m, 4H, 2×CH$_2$), 2.23-2.39 (m, 4H, 2×CH$_2$), 1.78-1.96 (m, 4H, 2×CH$_2$), 1.69-1.75 (m, 4H, 2×CH$_2$), 1.40-1.60 (m, 12H, 6×CH$_2$), 1.35-1.39 (m, 8H, 4×CH$_2$), 1.00 (t, J=7.2 Hz, 6H, 2×CH$_3$), 0.94-0.96 (m, 6H, 2×CH$_3$), −2.12 (br s, 2H, NH); $\delta_C$ (125 MHz; CDCl$_3$) 159.74 (α-C), 152.09 (α-C), 139.59 (α-C), 133.99 (α-C), 129.69 (β-C), 124.75 (β-C), 121.43 (β-C), 121.29 (β-C), 110.90 (meso-C), 73.01 (β-C), 38.10 (CH$_2$), 36.27 (CH$_2$), 35.01 (CH$_2$), 32.91 (CH$_2$), 32.03 (CH$_2$), 32.01 (CH$_2$), 30.44 (CH$_2$), 30.23 (CH$_2$), 22.95 (CH$_2$), 22.91 (CH$_2$), 14.35 (CH$_3$), 14.31 (CH$_3$); m/z (ET) 680.5023 (M$^+$, C$_{44}$H$_{64}$N$_4$O$_2$ requires 680.5029), 662 (100%), 646 (21), 609 (21), 591 (45).

1.1.2 Preparation of
5,10,15,20-tetrahexyl-7-dihydro-8-oxo-7,8-chlorin

In a typical experiment, trifluoroacetic acid (35 ml) was added to 5,10,15,20-tetrahexyl-7,8-dihydroxy-7,8-chlorin (548 mg, 0.80 mmol) and heated at 65° C. for 8 h. The reaction mixture was allowed to cool and poured into 300 ml ice/water. A sodium hydroxide solution (30%) was added until neutral. Then ethyl acetate (200 ml) was added, the organic layer was separated, washed with water (3×100 ml), dried over anhydrous sodium sulfate and the solvent was removed. The title compound 5,10,15,20-tetrahexyl-7-dihydro-8-oxo-7,8-chlorin was obtained after recrystallization from dichloromethane/methanol (524 mg, 98%).

5,10,15,20-Tetrahexyl-7-dihydro-8-oxo-7,8-chlorin

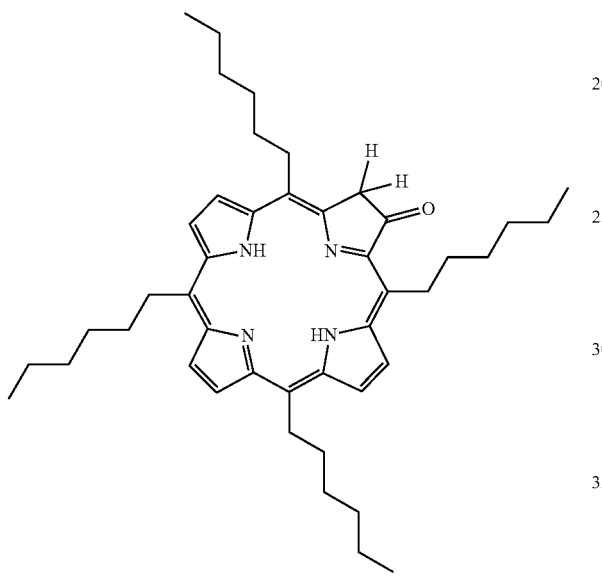

violet solid; $\lambda_{max}$ (CH$_2$Cl$_2$)/nm 419 ($\epsilon$/dm$^3$ mol$^{-1}$ cm$^{-1}$ 245000), 433 (193900), 534 (15900), 570 (19500), 604 (10100) and 659 (5800); $\delta_H$ (250 MHz; CDCl$_3$) 9.26-9.12 (m, 5H, β-H), 8.88-8.83 (m, 1H, β-H), 4.74-4.60 (m, 6H, 3×CH$_2$), 4.53 (s, 2H, β-H), 3.85-3.78 (m, 2H, CH$_2$), 2.56-2.33 (m, 4H, 2×CH$_2$), 2.17-1.98 (m, 4H, 2×CH$_2$), 1.85-1.31 (m, 24H, 12×CH$_2$), 0.99-0.91 (m, 12H, 4×CH$_3$), -2.23 (s, 1H, NH), -2.46 (s, 1H, NH); m/z (ESI) 663.4937 ([M+H]$^+$, C$_{44}$H$_{63}$N$_4$O$^+$ requires 663.4996).

1.1.3 Preparation of 5,10,15,20-tetrahexyl-7,8-dioxo-7,8-chlorin

In a typical experiment, Dess-Martin periodinane 15% solution in dichloromethane (1.6 g, 1.8 mmol) was added drop wise to a stirred solution of 5,10,15,20-tetrahexyl-7-dihydro-8-oxo-7,8-chlorin (250 mg, 0.37 mmol) in dichloromethane (15 ml), until the starting material was consumed. Then water (50 ml) was added, the organic layer was separated, washed with water (50 ml), dried over anhydrous sodium sulfate and the solvent was removed. The residue was purified by flash chromatography with dichloromethane/hexane 2:1 as eluent to yield the title compound 5,10,15,20-tetrahexyl-7,8-dioxo-7,8-chlorin (133 mg, 53%).

5,10,15,20-Tetrahexyl-7,8-dioxo-7,8-chlorin

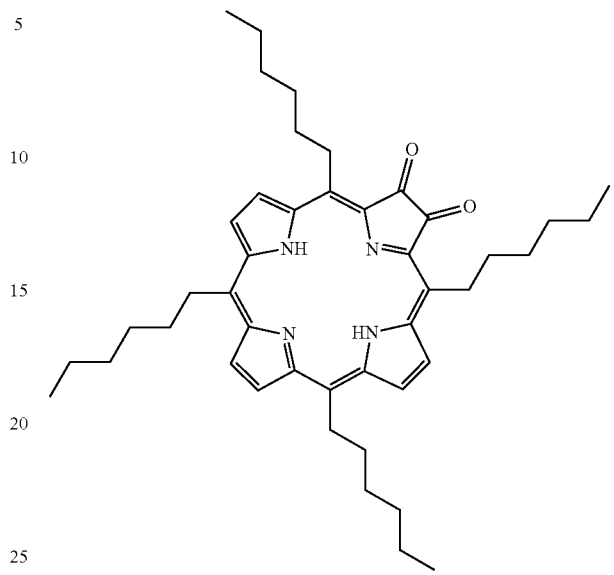

violet solid; $\lambda_{max}$ (CH$_2$Cl$_2$)/nm 407 ($\epsilon$/dm$^3$ mol$^{-1}$ cm$^{-1}$ 205600), 491 (16900), 715 (5300); $\delta_H$ (500 MHz; CDCl$_3$) 9.13-9.11 (m, 4H, β-H), 9.02-9.00 (m, 2H, β-H), 4.63-4.58 (m, 4H, 2×CH$_2$), 4.41-4.35 (m, 4H, 2×CH$_2$), 2.41-2.34 (m, 4H, 2×CH$_2$), 2.03-1.95 (m, 4H, 2×CH$_2$), 1.80-1.69 (m, 8H, 4×CH$_2$), 0.53-1.36 (m, 16H, 8×CH$_2$), 0.97-0.94 (m, 12H, 4×CH$_3$), -2.60 (s, 2H, NH); $\delta_C$ (126 MHz; CDCl$_3$) 189.22 (α-CO), 154.41 (α-C), 139.48 (α-C), 138.47 (α-C), 136.78 (α-C), 131.66 (β-C), 125.28 (AC), 124.76 (β-C), 122.80 (meso-C), 114.35 (meso-C), 38.35 (CH$_2$), 36.44 (CH$_2$), 35.56 (CH$_2$), 32.01 (CH$_2$), 31.97 (CH$_2$), 31.15 (CH$_2$), 30.41 (CH$_2$), 30.22 (CH$_2$), 22.94 (CH$_2$), 22.89 (CH$_2$), 14.34 (CH$_3$), 14.30 (CH$_3$); m/z (ESI) 677.4793 ([M+H]$^+$, C$_{44}$H$_{61}$N$_4$O$_2^+$ requires 677.4789); m/z (ESI) 675.4621 ([M−H]$^-$, C$_{44}$H$_{59}$N$_4$O$_2^-$ requires 675.4644).

1.2 Preparation of 5,10,15,20-tetrakis-(3-methoxyphenyl)-7,8-dioxo-7,8-chlorin (method A)

1.2.1 Preparation of 5,10,15,20-tetrakis-(3-methoxyphenyl)-7,8-dihydroxy-7,8-chlorin In a typical experiment, osmium tetroxide (1000 mg, 3.9 mmol) was added to a stirred solution of 5,10,15,20-tetrakis-(3-methoxyphenyl)-porphyrin (2500 mg, 3.4 mmol) in dichloromethane/pyridine 1:1 (340 ml). After stirring for 4 days, a saturated solution of sodium bisulfite in water/methanol 1:1 (150 ml) was added and the mixture was stirred for 18 h. The reaction mixture was filtered through Celite and dried over anhydrous sodium sulfate. The solvent was evaporated and the residue was purified by flash chromatography with dichloromethane/ethyl acetate 9:1 as eluent, followed by recrystallization from dichloromethane/aqueous methanol. The first band from the column contained starting material (793 mg, 32%) and the second band the title compound 5,10,15,20-tetrakis-(3-methoxyphenyl)-7,8-dihydroxy-7,8-chlorin (954 mg, 36%).

5,10,15,20-Tetrakis-(3-methoxyphenyl)-7,8-dihydroxy-7,8-chlorin

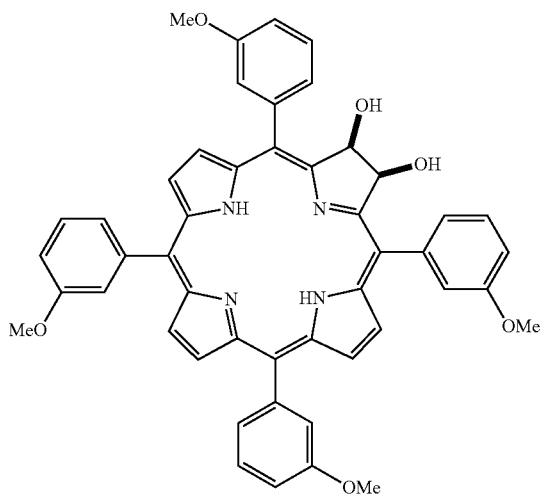 [SMILES: COc1cccc(-c2c3nc(c(-c4cccc(OC)c4)c4ccc([nH]4)c(-c4cccc(OC)c4)c4nc(c(-c5cccc(OC)c5)c5ccc2[nH]5)[C@@H](O)[C@H]4O)C=C3)c1]

violet solid; $\delta_H$ (400 MHz; CDCl$_3$) 8.69-8.66 (m, 2H, β-H), 8.51 (s, 2H, β-H), 8.40-8.32 (m, 2H, β-H), 7.77-7.44 (m, 12H, Ar), 7.31-7.21 (m, 4H, Ar), 6.44-6.34 (m, 2H, β-H), 3.97-3.91 (m, 12H, OCH$_3$) 3.26-3.19 (m, 2H, β-OH), −1.84 (s, 2H, NH).

1.2.2 Preparation of 5,10,15,20-tetrakis-(3-methoxyphenyl)-7-dihydro-8-oxo-7,8-chlorin In a typical experiment, trifluoroacetic acid (100 ml) was added to 5,10,15,20-tetrakis-(3-methoxyphenyl)-7,8-dihydroxy-7,8-chlorin (937 mg, 1.22 mmol) and heated at 65° C. for 8 h. The reaction mixture was allowed to cool and poured into 500 ml ice/water. A sodium hydroxide solution (30%) was added until neutral. Then ethyl acetate (300 ml) was added, the organic layer was separated, washed with water (3×150 ml), dried over anhydrous sodium sulfate and the solvent was removed. The title compound 5,10,15,20-tetrakis-(3-methoxyphenyl)-7-dihydro-8-oxo-7,8-chlorin was obtained after recrystallization from dichloromethane/methanol (899 mg, 98%).

5,10,15,20-Tetrakis-(3-methoxyphenyl)-7-dihydro-8-oxo-7,8-chlorin

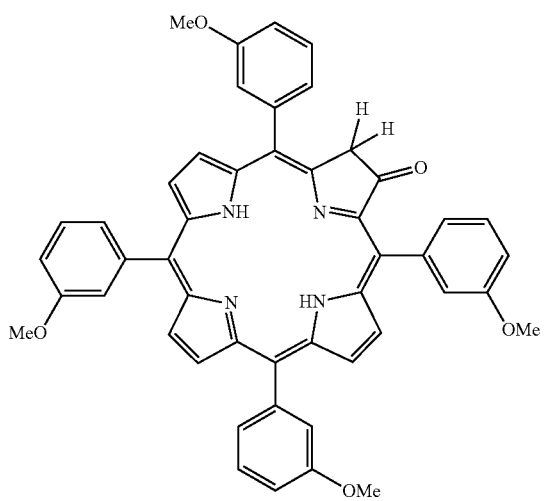 [SMILES: COc1cccc(-c2c3nc(c(-c4cccc(OC)c4)c4ccc([nH]4)c(-c4cccc(OC)c4)c4nc(c(-c5cccc(OC)c5)c5ccc2[nH]5)CC4=O)C=C3)c1]

violet solid; mp: >300° C.; m/z (ESI) 751.2936 ([M+H]$^+$, C$_{48}$H$_{39}$N$_4$O$_5$$^+$ requires 751.2915); no NMR spectroscopy was carried out, because of keto-enol tautomeric mixtures.

1.2.3 Preparation of 5,10,15,20-tetrakis-(3-methoxyphenyl)-7,8-dioxo-7,8-chlorin In a typical experiment, Dess-Martin periodinane 15% solution in dichloromethane (1 g, 1.1 mmol) was added drop wise within 2 h to a stirred solution of 5,10,15,20-tetrakis-(3-methoxyphenyl)-7-dihydro-8-oxo-7,8-chlorin (160 mg, 0.21 mmol) in dichloromethane (20 ml) and stirred for further 3 h. Then water (50 ml) was added, the organic layer was separated, washed with water (50 ml), dried over anhydrous sodium sulfate and the solvent was removed. The residue was purified by flash chromatography with dichloromethane/ethyl acetate 99:1 as eluent to yield the title compound 5,10,15,20-tetrakis-(3-methoxyphenyl)-7,8-dioxo-7,8-chlorin (123 mg, 75%).

5,10,15,20-Tetrakis-(3-methoxyphenyl)-7,8-dioxo-7,8-chlorin

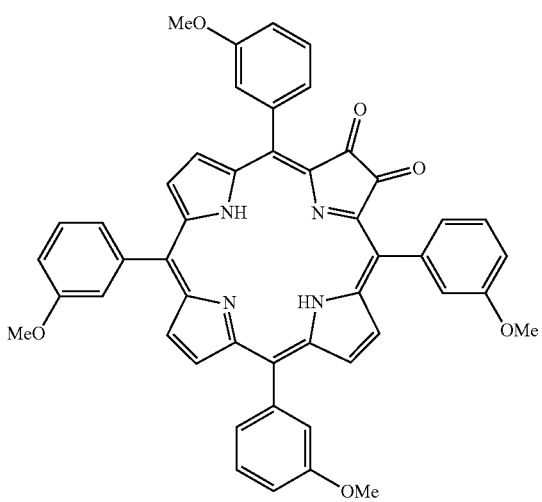 [SMILES: COc1cccc(-c2c3nc(c(-c4cccc(OC)c4)c4ccc([nH]4)c(-c4cccc(OC)c4)c4nc(c(-c5cccc(OC)c5)c5ccc2[nH]5)C(=O)C4=O)C=C3)c1]

violet solid; $\lambda_{max}$ (CH$_2$Cl$_2$)/nm 406 ($\epsilon$/dm$^3$ mol$^{-1}$ cm$^{-1}$ 104600); $\delta_H$ (250 MHz; CDCl$_3$) 8.81 (dd, $^4$J=1.0 Hz, $^3$J=5.0 Hz, 2H, β-H), 8.68 (dd, $^4$J=1.4 Hz, $^3$J=5.0 Hz, 2H, β-H), 8.62 (s, 2H, β-H), 7.77-7.45 (m, 12H, Ar), 7.35-7.27 (m, 4H, Ar), 3.97 (s, 6H, OCH$_3$), 3.94 (s, 6H, OCH$_3$), −2.04 (br m, 2H, NH); m/z (ESI) 765.2729 ([M+H]$^+$, C$_{48}$H$_{37}$N$_4$O$_6$$^+$ requires 765.2708).

1.3 Preparation of 5,10,15,20-tetrakis-(3-methoxyphenyl)-7,8-dioxo-7,8-chlorin (method B)

1.3.1 Preparation of Cu(II)-5,10,15,20-tetrakis-(3-methoxyphenyl)-7-nitro-porphyrin In a typical experiment, Cu(NO$_3$)$_2$ 2.5; H$_2$O (500 mg, 2.2 mmol) dissolved in a mixture of acetic anhydride (50 ml) and acetic acid (10 ml) was added to a solution of 5,10,15,20-tetrakis-(3-methoxyphenyl)-porphyrin (600 mg, 0.8 mmol) in dichloromethane (500 ml) and the mixture was refluxed for 10 h. Then, the solvents were removed and the residue was purified by flash chromatography with dichloromethane/ethyl acetate 99:1. The title compound Cu(II)-5,10,15,20-tetrakis-(3-methoxyphenyl)-7-nitro-porphyrin was obtained after recrystallization from dichloromethane/methanol (610 mg, 91%).

Cu(II)-5,10,15,20-tetrakis-(3-methoxyphenyl)-7-nitro-porphyrin

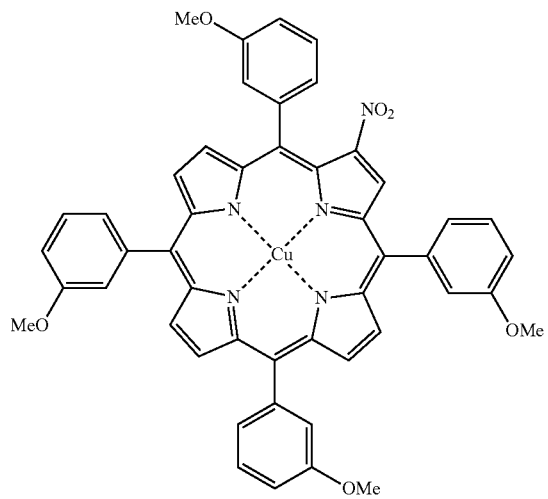

grey solid; mp: 200° C.; m/z (ESI) 840.1970 ([M]$^+$, $C_{48}H_{35}CuN_5O_6^+$ requires 840.1878.

1.3.2 Preparation of 5,10,15,20-tetrakis-(3-methoxyphenyl)-7-dihydro-8-oxo-7,8-chlorin In a typical experiment, sodium hydride (200 mg, 5 mmol) was added to dry dimethyl sulfoxide (250 ml). The mixture was heated under argon at 75° C. for 30 min and then E-benzaldehyde oxime (1.5 ml, 11 mmol) was added. To the resultant yellow mixture solid Cu(II)-5,10,15,20-tetrakis-(3-methoxyphenyl)-7-nitro-porphyrin (1.1 g, 1.3 mmol) was added. After 120 min the mixture was cooled in an ice bath and diluted with dichloromethane (300 ml). The organic layer was washed with water (5×200 ml), dried over anhydrous sodium sulfate and the solvent was removed. The crude product was dissolved in a mixture of trifluoroacetic acid/conc. sulfuric acid 10:1 (44 ml), and after 8 min ethyl acetate (200 ml) and water (200 ml) were added as well as sodium hydroxide 30% solution until neutral. The organic layer was washed with water (4×200 ml), dried over anhydrous sodium sulfate and the solvent was removed. The residue was purified by flash chromatography with dichloromethane/ethyl acetate 99:1 as eluent. The title compound 5,10,15,20-tetrakis-(3-methoxyphenyl)-7-dihydro-8-oxo-7,8-chlorin was obtained after recrystallization from dichloromethane/methanol (501 mg, 50% over 2 steps).

Spectroscopic data given in 1.2.2

1.3.3 Preparation of 5,10,15,20-tetrakis-(3-methoxyphenyl)-7,8-dioxo-7,8-chlorin compare 1.2.3

Example 2

Preparation of Trifluoromethyl β-Substituted Chlorins 2.1. Preparation of 5,10,15,20-tetrahexyl-7-trifluoromethyl-7,8-dihydroxy-7,8-chlorin In a typical experiment, a solution of 5,10,15,20-tetrahexyl-7,8-dioxo-7,8-chlorin (50 mg, 0.07 mmol) in dry tetrahydrofuran (3 ml) under argon atmosphere was cooled to −35° C. (Trifluoromethyl)trimethylsilane (50 μl, 0.38 mmol) and tetrabutylammonium fluoride trihydrate (10 mg, 0.03 mmol) were added and the mixture was stirred for 20 min. In order to remove the trimethylsilyl group more tetrabutylammonium fluoride trihydrate (50 mg, 0.3 mmol) was added and the reaction mixture was stirred until complete conversion. Then, water (25 ml) and dichloromethane (25 ml) were added, the organic layer was separated, washed with water (25 ml), dried over anhydrous sodium sulfate and the solvent was removed. The residue was purified by flash chromatography with dichloromethane/hexane 1:1 as eluent to yield 5,10,15,20-tetrahexyl-7-trifluouromethyl-7-hydroxy-8-oxo-7,8-chlorin. 5,10,15,20-tetrahexyl-7-trifluouromethyl-7-hydroxy-8-oxo-7,8-chlorin (25 mg, 0.03 mmol) was dissolved in dichloromethane/methanol 9:1 (3 ml) and cooled to 0° C. Sodium borohydride was added (5 mg, 0.13 mmol) and the mixture was stirred until the starting material was consumed. Then, water (10 ml) and dichloromethane (10 ml) were added, the organic layer was separated, washed with water (10 ml), dried over anhydrous sodium sulfate and the solvent was removed. The title compound 5,10,15,20-tetrahexyl-7-trifluoromethyl-7,8-dihydroxy-7,8-chlorin was obtained after recrystallization from dichloromethane/methanol (21 mg, 60% over 2 steps).

5,10,15,20-Tetrahexyl-7-trifluoromethyl-7,8-dihydroxy-7,8-chlorin

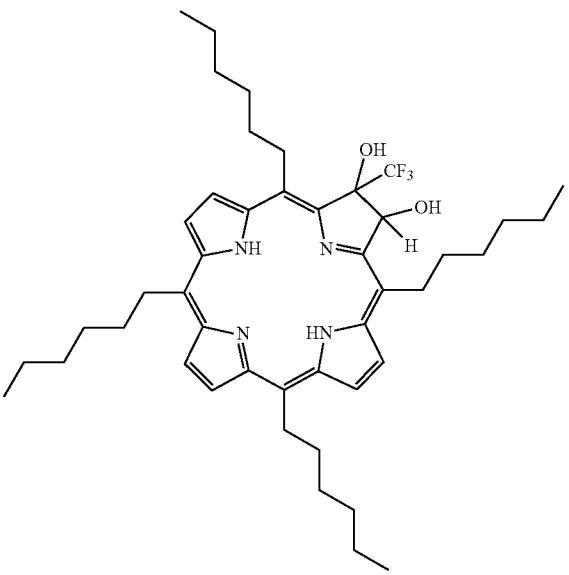 [SMILES: CCCCCCc1c2nc(c(CCCCCC)c3ccc([nH]3)c(CCCCCC)c3nc(c(CCCCCC)c4ccc1[nH]4)C(O)C3(O)C(F)(F)F)C=C2]

violet solid; mp: 120-125° C.; $\lambda_{max}(CH_2Cl_2)$/nm 410 (ε/dm$^3$ mol$^{-1}$ cm$^{-1}$ 220300), 432 (149100), 533 (16600), 562 (25100), 599 (12100), 653 (17400); $\delta_H$ (500 MHz; CDCl$_3$)

9.22-9.20 (m, 2H, β-H), 9.13 (d, J=4.6 Hz, 1H, β-H), 9.09 (d, J=4.6 Hz, 1H, β-H), 9.03 (d, J=5.0 Hz, 1H, β-H), 8.97 (d, J=5.1 Hz, 1H, β-H), 6.96-6.93 (m, 1H, β-H), 4.72-4.56 (m, 4H, 2×CH$_2$), 4.46-4.35 (m, 3H, CH$_2$, CH$_A$), 4.28-4.20 (m, 1H, CH$_B$), 3.93 (br s, 1H, β-OH), 2.93-2.84 (m, 1H, β-OH), 2.44-2.36 (m, 4H, 2×CH$_2$), 2.33-2.16 (m, 2H, CH$_2$), 2.02-1.95 (m, 2H, CH$_2$), 1.82-1.71 (m, 6H, 3×CH$_2$), 1.61-1.26 (m, 18H, 9×CH$_1$), 0.99-0.88 (m, 12H, 4×CH$_3$), −1.51 (br s, 2H, NH), δ$_C$ (126 MHz; CDCl$_3$) 155.25 (α-C), 153.25 (α-C), 153.15 (α-C), 149.30 (α-C), 140.58 (α-C), 140.30 (α-C), 135.02 (α-C), 134.24 (α-C), 130.41 (β-C), 129.88 (β-C), 125.80 (β-C), 124.95 (β-C), 123.30 (mesa-C), 122.85 (β-C), 122.52 (β-C), 121.49 (mesa-C), 113.78 (mesa-C), 109.89 (meso-C), 89.18 (β-C), 38.15 (CH$_2$), 38.09 (CH$_2$), 38.04 (CH$_2$), 36.47 (CH$_2$), 35.55 (CH$_2$), 35.12 (CH$_2$), 33.04 (CH$_2$), 32.87 (CH$_2$), 32.04 (CH$_2$), 31.96 (CH$_2$), 30.62 (CH$_2$), 30.44 (CH$_2$), 30.39 (CH$_2$), 30.21 (CH$_2$), 23.00 (CH$_2$), 22.89 (CH$_2$), 14.30 (CH$_3$), 14.25 (CH$_3$); δ$_F$ (471 MHz; CDCl$_3$) −72.65 (CF$_3$); m/z (ESI) 749.4955 ([M+H]$^+$, C$_{45}$H$_{64}$F$_3$N$_4$O$_2^+$ requires 749.4976).

2.2 Preparation of 5,10,15,20-tetrakis-(3-methoxyphenyl)-7,8-dihydroxy-7,8-bis-(trifluoromethyl)-7,8-chlorin In a typical experiment, a solution of 5,10,15,20-tetrakis-(3-methoxyphenyl)-7,8-dioxo-7,8-chlorin (100 mg, 0.13 mmol), in dry tetrahydrofuran (7 ml), under argon atmosphere, was cooled to −40° C. (Trifluoromethyl)trimethylsilane (350 W, 2.66 mmol) and tetrabutyl ammoniumfluoride trihydrate (10 mg, 0.03 mmol) were added and the mixture was stirred for 8 h. In order to remove the trimethylsilyl groups, more tetrabutylammonium fluoride trihydrate (100 mg, 0.3 mmol) was added and the reaction mixture was stirred until complete conversion. Then, water (40 ml) and dichloromethane (50 ml) were added, the organic layer was separated, washed with water (40 ml), dried over anhydrous sodium sulfate and the solvent was removed. The residue was purified by flash chromatography with dichloromethane/ethyl acetate 99:1 as eluent. The title compound 5,10,15,20-tetrakis-(3-methoxyphenyl)-7,8-dihydroxy-7,8-bis-(trifluoromethyl)-7,8-chlorin was obtained after recrystallization from dichloromethane/methanol. (92 mg, 78%).

5,10,15,20-Tetrakis-(3-methoxyphenyl)-7,8-dihydroxy-7,8-bis-(trifluoro-methyl)-7,8-chlorin violet solid; mp: 177° C., λ$_{max}$ (CH$_2$Cl$_2$)/nm 409 (ε/dm$^3$ mol$^{-1}$ cm$^{-1}$ 135300), 518 (9300), 548 (9200), 599 (4200), 653 (17300); 34500 MHz; CDCl$_3$) 8.63-8.61 (m, 2H, β-H), 8.47 (s, 2H, β-H), 8.03-8.00 (m, 2H, β-H), 7.89-7.77 (m, 4H, Ar), 7.68-7.43 (m, 6H, Ar), 7.35-7.26 (m, 6H, Ar), 4.13-4.11 (m, 1H, β-OH), 4.02-4.01 (m, 1H, β-OH), 4.00-3.98 (br m, 3H, OCH$_3$), 3.98-3.97 (m, 3H, OCH$_3$), 3.91-3.89 (br m, 3H, OCH$_3$) 3.87-3.85 (m, 3H, OCH$_3$), −1.48-1.52 (br m, 2H, NH); δ$_C$ (126 MHz; CDCl$_3$) 159.02 (Ar), 158.20 (Ar), 153.63 (α-C), 149.54 (α-C), 149.17 (α-C), 142.55 (Ar), 141.55 (α-C), 138.98 (Ar), 138.82 (Ar), 136.03 (α-C), 133.24 (AC), 128.97 (Ar), 128.48 (AC), 128.38 (Ar), 127.80 (Ar), 127.46 (Ar), 126.91 (Ar), 125.87 (Ar), 125.09 (β-C), 124.53 (β-C), 124.46 (AC), 120.63 (Ar), 119.81 (Ar), 119.29 (Ar), 115.40 (Ar), 113.84 (Ar), 111.57 (meso-C), 111.45 (meso-C), 55.61 (OCH$_3$), 55.50 (OCH$_3$); δ$_F$ (471 MHz; CDCl$_3$) −73.92 (CF$_3$), −73.94 (CF$_3$), −74.12 (CF$_3$), −74.15 (CF$_3$); m/z (ESI) 905.2774 ([M+H]$^+$, C$_{50}$H$_{39}$F$_6$N$_4$O$_6^+$ requires 905.2768).

2.3 Preparation of 5,10,15,20-tetrakis-(3-hydroxyphenyl)-7,8-dihydroxy-7,8-bis-(trifluoromethyl)-7,8-chlorin In a typical experiment, a solution of 5,10,15,20-tetrakis-(3-methoxyphenyl)-7,8-dihydroxy-7,8-bis-(trifluoromethyl)-7,8-chlorin (80 mg, 0.09 mmol), in dry dichloromethane (30 ml), under argon atmosphere, was cooled to −50° C. A boron tribromide solution (1 M, 1.6 ml) in dichloromethane was added dropwise over a period of 10 min. The reaction mixture was allowed to warm up slowly to room temperature and stirred for 18 h. Then, water (100 ml) and ethyl acetate (100 ml) were added as well as sodium hydroxide solution 30% until neutral. The organic layer was separated, washed with water (2×100 ml), dried over anhydrous sodium sulfate and the solvent was removed. The residue was purified by flash chromatography with dichloromethane/methanol 95:5 as eluent. Further purification was achieved by column chromatography with C$_{18}$ reversed phase silica gel using methanol/water 95:5 as eluent. The title compound 5,10,15,20-tetrakis-(3-hydroxyphenyl)-7,8-dihydroxy-7,8-bis-(trifluoromethyl)-7,8-chlorin was obtained after recrystallization from dichloromethane/aqueous methanol. (65 mg, 87%).

5,10,15,20-Tetrakis-(3-hydroxyphenyl)-7,8-dihydroxy-7,8-bis-(trifluoro-methyl)-7,8-chlorin

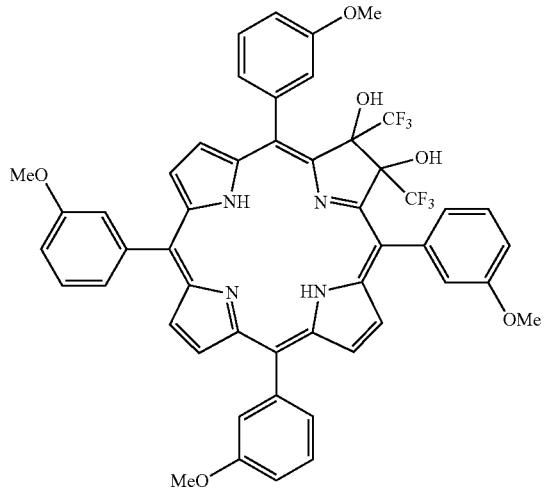 [SMILES: COc1cccc(-c2c3nc(c(-c4cccc(OC)c4)c4ccc([nH]4)c(-c4cccc(OC)c4)c4nc(c(-c5cccc(OC)c5)c5ccc2[nH]5)C(O)(C(F)(F)F)C4(O)C(F)(F)F)C=C3)c1]

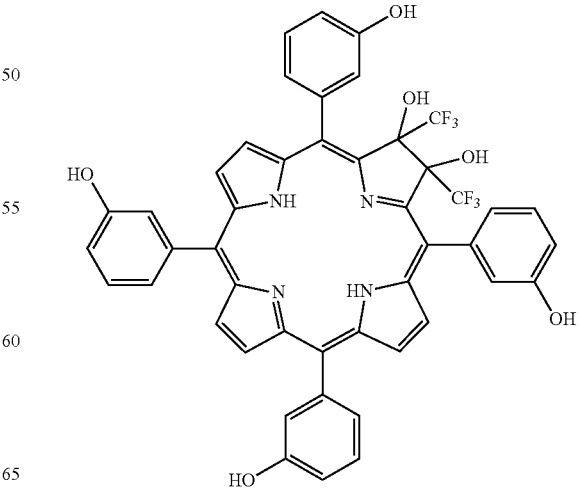

violet solid; mp: >300° C.; $\lambda_{max}((CH_3)_2CO)$/nm 407 ($\epsilon$/dm³ mol⁻¹ cm⁻¹ 166900), 518 (15200), 547 (15600), 599 (7700), 653 (27600); $\delta_H$ (700 MHz; $(CD_3)_2CO$) 8.82-8.66 (m, 6H, 2×β-H, 4×Ar—OH), 8.50 (s, 2H, β-H), 8.14-8.12 (m, 2H, β-H), 7.81-7.11 (m, 16H, Ar), 5.75-5.57 (m, 2H, β-OH), −1.38-−1.42 (m, 2H, NH); $\delta_C$ (176 MHz; $(CD_3)_2CO$) 156.35 (Ar), 156.30 (Ar), 156.05 (Ar), 155.99 (Ar), 155.46 (Ar), 155.41 (Ar), 153.44 (α-C), 150.47 (α-C), 150.39 (α-C), 150.28 (α-C), 150.19 (α-C), 142.42 (Ar), 142.39 (Ar), 141.68 (α-C), 141.61 (α-C), 141.58 (α-C), 141.51 (α-C), 139.91 (Ar), 139.87 (Ar), 135.75 (α-C), 132.86 (β-C), 128.15 (Ar), 128.12 (β-C), 128.02 (Ar), 127.96 (Ar), 127.90 (Ar), 127.52 (Ar), 127.45 (Ar), 126.21 (Ar), 126.00 (Ar), 125.53 (β-C), 125.48 (Ar), 125.43 (Ar), 125.38 (Ar), 125.33 (Ar), 125.28 (Ar), 125.23 (Ar), 124.37 (meso-C), 124.30 (meso-C), 121.95 (Ar), 121.39 (Ar), 121.35 (Ar), 121.16 (Ar), 115.58 (Ar), 115.52 (Ar), 115.47 (Ar), 115.40 (Ar), 115.14 (meso-C), 112.52 (Ar), 112.44 (Ar), 112.28 (Ar), 112.22 (Ar), 90.4-89.8 (m, β-C); $\delta_F$ (471 MHz; $CD_3OD$) −75.02 ($CF_3$), −75.05 ($CF_3$); m/z (ESI) 849.2163 ([M+]⁺, $C_{46}H_{31}F_6N_4O_6^+$ requires 849.2142).

Example 3

Preparation of Alkyl, Alkenyl and Alkynyl β-Substituted Chlorins 3.1 Preparation of 5,10,15,20-tetrakis-(3-methoxyphenyl)-7,8-allyl-7,8-dihydroxy-7,8-chlorin In a typical experiment, a solution of 5,10,15,20-tetrakis-(3-methoxyphenyl)-7,8-dioxo-7,8-chlorin (102 mg, 0.13 mmol), in dry tetrahydrofuran (10 ml), under argon atmosphere, was cooled to −50° C. Allylmagnesium chloride (2 M, 300 μl) in tetrahydrofuran was added and the mixture was stirred for 15 min. Then, water (80 ml) and dichloromethane (100 ml) were added, the organic layer was separated, washed with water (80 ml), dried over anhydrous sodium sulfate and the solvent was removed. The residue was purified by flash chromatography with dichloromethane/ethyl acetate 99:1 as eluent. The title compound 5,10,15,20-tetrakis-(3-methoxyphenyl)-7,8-allyl-7,8-dihydroxy-7,8-chlorin was obtained after recrystallization from dichloromethane/methanol (24 mg, 21%).

5,10,15,20-Tetrakis-(3-methoxyphenyl)-7,8-allyl-7,8-dihydroxy-7,8-chlorin

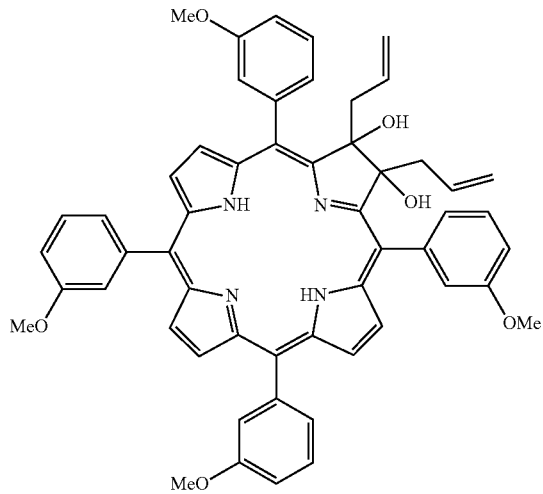 [SMILES: C=CCC1(O)c2nc(c(-c3cccc(OC)c3)c3ccc([nH]3)c(-c3cccc(OC)c3)c3nc(c(-c4cccc(OC)c4)c4ccc([nH]4)c2-c2cccc(OC)c2)C=C3)C1(O)CC=C]

violet solid; mp: 175° C.; $\lambda_{max}$ ($CH_2Cl_2$)/nm 418 ($\epsilon$/dm³ mol⁻¹ cm⁻¹ 187700), 518 (15500), 546 (10700), 600 (5900), 654 (26400); $\delta_H$ (500 MHz; $CDCl_3$) 8.61-8.59 (m, 2H, β-H), 8.46 (s, 2H, β-H), 8.09-8.06 (m, 2H, β-H), 7.94-7.77 (m, 4H, Ar), 7.67-7.45 (m, 6H, Ar), 7.28-7.11 (m, 6H, Ar), 4.94-4.80 (m, 2H, alkyl), 4.65-4.53 (m, 2H, alkyl), 4.18-4.09 (m, 2H, alkyl), 4.00 (s, 3H, $OCH_3$), 3.97 (s, 3H, $OCH_3$), 3.91 (s, 3H, $OCH_3$), 3.86 (s, 3H, $OCH_3$), 3.21-3.09 (m, 2H, alkyl), 2.83-2.75 (m, 2H, alkyl), 2.69-2.67 (m, 1H, β-OH), 2.60-2.58 (m, 1H, β-OH), −1.57 (s, 2H, NH); m/z (ESI) 849.3671 ([M+H]⁺, $C_{54}H_{49}N_4O_6^+$ requires 849.3647).

3.2 Preparation of 5,10,15,20-tetrakis-(3-methoxyphenyl)-7,8-diethinyl-7,8-dihydroxy-7,8-chlorin In a typical experiment, a solution of 5,10,15,20-tetrakis-(3-methoxyphenyl)-7,8-dioxo-7,8-chlorin (200 mg, 0.26 mmol) in dry tetrahydrofuran (10 ml) under argon atmosphere was cooled to −45° C. Ethinylmagnesium chlorid (0.6 M, 2 ml) in tetrahydrofuran was added and the mixture was stirred for 2.5 h. Then, water (80 ml) and dichloromethane (100 ml) were added, the organic layer was separated, washed with water (80 ml), dried over anhydrous sodium sulfate and the solvent was removed. The residue was purified by flash chromatography with dichloromethane/ethyl acetate 99:1 as eluent. The title compound 5,10,15,20-tetrakis-(3-methoxyphenyl)-7,8-diethinyl-7,8-dihydroxy-7,8-chlorin was obtained after recrystallization from dichloromethane/methanol (120 mg, 56%).

5,10,15,20-Tetrakis-(3-methoxyphenyl)-7,8-diethinyl-7,8-dihydroxy-7,8-chlorin

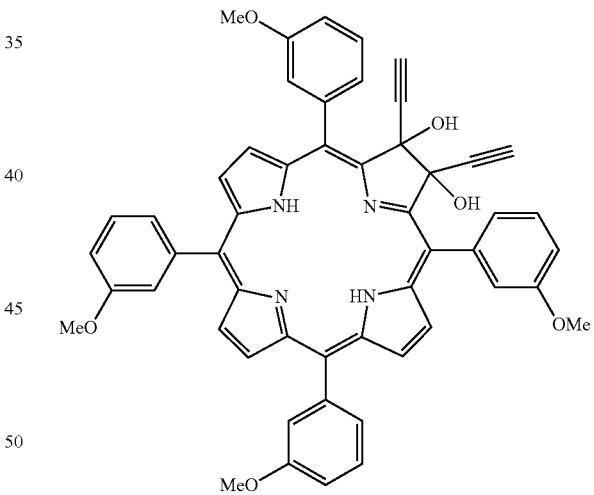

violet solid; mp: 240° C.; $\lambda_{max}$ ($CH_2O_2$)/nm 415 ($\epsilon$/dm³ mol⁻¹ cm⁻¹ 194200), 518 (13700), 545 (13600), 594 (7700), 645 (15800); $\delta_H$ (250 MHz; $CDCl_3$) 8.77-8.46 (m, 6H, β-H), 7.83-7.17 (m, 16H, Ar), 4.01-3.86 (m, 12H, $OCH_3$), 3.61-3.52 (m, 2H, C≡CH), 2.62-2.46 (m, 2H, β-OH), −2.02-2.19 (s, 2H, NH); m/z (ESI) 817.3007 ([M+H]⁺, $C_{52}H_{41}N_4O_6^+$ requires 817.3021).

3.3 Preparation of 5,10,15,20-tetrakis-(3-methoxyphenyl)-7,8-dihexyl-7,8-dihydroxy-7,8-chlorin In a typical experiment, a solution of 5,10,15,20-tetrakis-(3-methoxyphenyl)-7,8-dioxo-7,8-chlorin (50 mg, 0.07 mmol) in dry tetrahydrofuran (5 ml) under argon atmosphere was cooled to −45° C. Hexylmagnesium bromide in diethyl ether (2 M, 500 µl) was added and the mixture was stirred for 3 h. Then, water (40 ml) and dichloromethane (50 ml) were added, the organic layer was separated, washed with water (40 ml), dried over anhydrous sodium sulfate and the solvent was removed. The residue was purified by flash chromatography with dichloromethane as eluent. The title compound 5,10,15,20-tetrakis-(3-methoxyphenyl)-7,8-dihexyl-7,8-dihydroxy-7,8-chlorin was obtained after recrystallization from dichloromethane/methanol (32 mg, 53%).

5,10,15,20-Tetrakis-(3-methoxyphenyl)-7,8-dihexyl-7,8-dihydroxy-7,8-chlorin

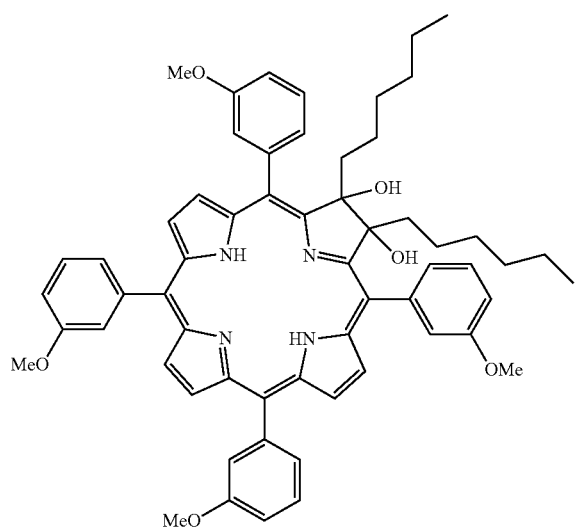 [SMILES: CCCCCCC1(O)c2nc(c(-c3cccc(OC)c3)c3ccc([nH]3)c(-c3cccc(OC)c3)c3nc(c(-c4cccc(OC)c4)c4ccc([nH]4)c2-c2cccc(OC)c2)C=C3)C1(O)CCCCCC]

violet solid; mp: 205° C.; $\lambda_{max}$ (CH$_2$Cl$_2$)/nm 418 ($\epsilon$/dm$^3$ mol$^{-1}$ cm$^{-1}$ 176100), 518 (14600), 546 (9900), 601 (5300), 655 (26900); $\delta_H$(500 MHz; CDCl$_3$) 8.60-8.58 (m, 2H, β-H), 8.45 (s, 2H, β-H), 8.05-8.01 (m, 2H, β-H), 7.94-7.91 (m, 1H, Ar), 7.88-7.85 (m, 1H, Ar), 7.82-7.75 (m, 2H, Ar), 7.67-7.63 (m, 1H, Ar), 7.62-7.50 (m, 4H, Ar), 7.49-7.44 (m, 1H, Ar), 7.28-7.20 (m, 4H, Ar), 7.15-7.13 (m, 1H, Ar), 7.08-7.05 (m, 1H, Ar), 4.00-3.99 (m, 3H, OCH$_3$), 3.98-3.95 (br m, 3H, OCH$_3$), 3.92-3.89 (br m, 3H, OCH$_3$), 3.84-3.83 (m, 3H, OCH$_3$), 2.52-2.41 (m, 2H, CH$_2$), 2.32-2.31 (m, 1H, β-OH), 2.22-2.20 (m, 1H, β-OH), 1.88-1.77 (m, 2H, CH$_2$), 1.25-1.10 (m, 2H, CH$_2$), 0.90-0.75 (m, 7H, 3×CH$_2$, CH$_A$), 0.74-0.58 (m, 6H, 3×CH$_2$), 0.53-0.48 (m, 6H, 2×CH$_3$), −0.40-0.60 (m, 1H, CH$_B$), −1.51 (s, 2H, NH); $\delta_C$ (126 MHz; CDCl$_3$) 158.27 (Ar), 152.60 (α-C), 143.1.4 (Ar), 142.01 (α-C), 141.25 (Ar), 135.34 (α-C), 132.31 (β-C), 128.06 (β-C), 127.99 (Ar), 126.93 (Ar), 126.48 (Ar), 124.31 (β-C), 122.89 (meso-C), 120.24 (Ar), 119.79 (Ar), 119.72 (Ar), 119.53 (Ar), 114.43 (Ar), 113.83 (Ar), 1133.62 (Ar), 111.36 (meso-C), 90.37 (β-C), 55.54 (OCH$_3$), 55.36 (OCH$_3$), 41.84 (CH$_2$), 41.80 (CH$_2$), 31.26 (CH$_2$), 31.20 (CH$_2$), 29.56 (CH$_2$), 29.44 (CH$_2$), 24.30 (CH$_2$), 24.24 (CH$_2$), 22.38 (CH$_2$), 22.37 (CH$_2$), 13.84 (CH$_3$), 13.81 (CH$_3$); m/z (ESI) 937.4870 ([M+H]$^+$, C$_{60}$H$_{65}$N$_4$O$_6^+$ requires 937.4899).

3.4 Preparation of 5,10,15,29-tetrakis-(3-hydroxyphenyl)-7,8-dihexyl-7,8-dihydroxy-7,8-chlorin In a typical experiment, a solution of 5,10,15,20-tetrakis-(3-methoxyphenyl)-7,8-dihexyl-7,8-dihydroxy-7,8-chlorin (15 mg, 0.02 mmol), in dry dichloromethane (5 ml) under argon atmosphere, was cooled to −60° C. A boron tribromide solution (1 M, 300 µl) in dichloromethane was added dropwise over a period of 10 min. The reaction mixture was allowed to warm up slowly to room temperature and stirred for 18 h. Then, water (20 ml) and ethyl acetate (50 ml) were added as well as sodium hydroxide solution 30% until neutral. The organic layer was separated, washed with water (2×50 ml), dried over anhydrous sodium sulfate and the solvent was removed. The residue was purified by flash chromatography with dichloromethane/methanol 95:5 as eluent. Further purification was achieved by column chromatography with C$_{18}$ reversed phase silica gel, using methanol/water 95:5 as eluent. The title compound 5,10,15,20-tetrakis-(3-hydroxyphenyl)-7,8-dihexyl-7,8-dihydroxy-7,8-chlorin was obtained after recrystallization from dichloromethane/aqueous methanol (12 mg, 85%).

5,10,15,20-Tetrakis-(3-hydroxyphenyl)-7,8-dihexyl-7,8-dihydroxy-7,8-chlorin

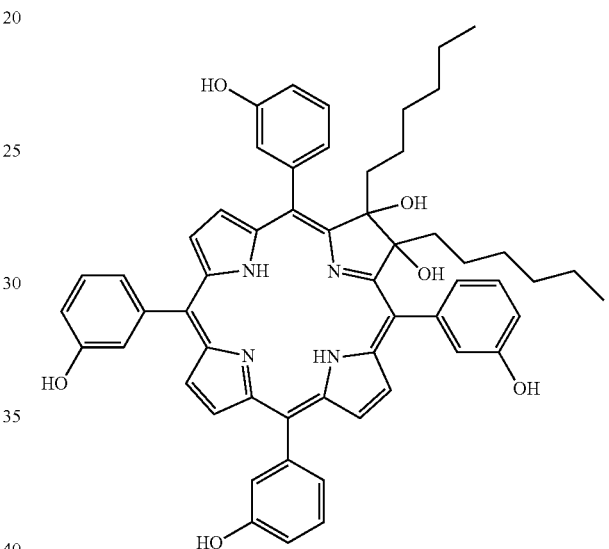

violet solid; mp: 180° C.; $\lambda_{max}$((CH$_3$)$_2$CO)/nm 418 ($\epsilon$/dm$^3$ mol$^{-1}$ cm$^{-1}$ 116800), 518 (10800), 544 (7400), 600 (4600), 653 (21900); $\delta_H$ (250 MHz; (CD$_3$)$_2$CO) 8.80-8.72 (m, 3H, Ar—OH), 8.64 (d, J=5.0 Hz, 2H, β-H), 8.64 (s, 1H, Ar—OH), 8.43 (s, 2H, g-H), 8.10 (d, J=5.0 Hz, 2H, β-H), 7.90-6.99 (m, 16H, Ar), 3.32-3.29 (m, 1H, β-OH), 3.25-3.23 (m, 1H, β-OH), 2.62-2.45 (m, 2H, CH$_2$), 1.98-1.90 (m, 2H, CH)), 0.90-0.57 (m, 14H, 7×CH$_2$), 0.50-0.41 (m, 6H, 2×CH$_3$), −0.43-0.57 (m, 2H, CH$_2$), −1.45 (s, 2H, NH); m/z (ESI) 881.4264 ([M+H]$^+$, C$_{56}$H$_{57}$N$_4$O$_6^+$ requires 881.4273).

Example 4

Preparation of 3,5-bis-(trifluoromethyl)-phenyl β-substituted chlorins 4.1 Preparation of 5,10,15,20-tetrakis-(3-methoxyphenyl)-7,8-bis-[3,5-bis-(trifluoro-methyl)-phenyl]-7,8-dihydroxy-7,8-chlorin In a typical experiment, a solution of 5,10,15,20-tetrakis-(3-methoxyphenyl)-7,8-dioxo-7,8-chlorin (300 mg, 0.39 mmol), in dry tetrahydrofuran (30 ml) under argon atmosphere, was cooled to −50° C. 3,5-Bis-(trifluoromethyl)-phenylmagnesium bromide in tetrahydrofuran (0.5 M, 3.9 ml) was added and the mixture was stirred for 3 h. Then, water (200 ml) and ethyl acetate (200 ml) were added, the organic layer was separated, washed with water (200 ml), dried over anhydrous sodium sulfate and the solvent was removed. The residue was purified by flash chromatography with dichloromethane as eluent. The title compound 5,10,15,20-tetrakis-(3-methoxyphenyl)-7,8-bis-[3,5-bis-(trifluoromethyl)-phenyl]-7,8-dihydroxy-7,8-chlorin was obtained after recrystallization from dichloromethane/aqueous methanol (203 mg, 44%).

5,10,15,20-Tetrakis-(3-methoxyphenyl)-7,8-bis-[3,5-bis-(trifluoromethyl)-phenyl]-7,8-dihydroxy-7,8-chlorin

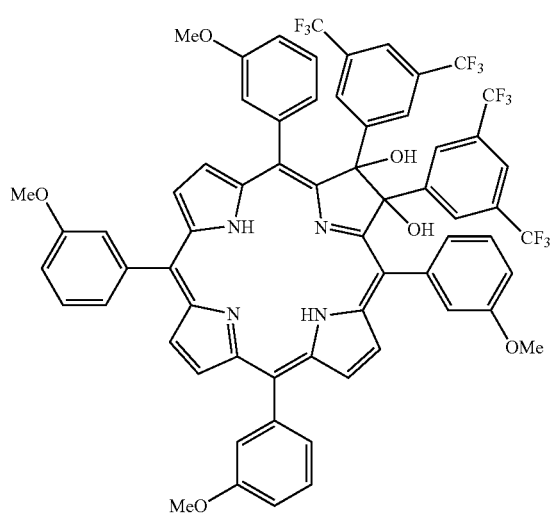 [SMILES: COc1cccc(-c2c3nc(c(-c4cccc(OC)c4)c4ccc([nH]4)c(-c4cccc(OC)c4)c4nc(c(-c5cccc(OC)c5)c5ccc2[nH]5)C(O)(c2cc(C(F)(F)F)cc(C(F)(F)F)c2)C4(O)c2cc(C(F)(F)F)cc(C(F)(F)F)c2)C=C3)c1]

violet solid; mp: 170° C.; $\lambda_{max}$ ($CH_2Cl_2$)/nm 414 ($\epsilon$/dm$^3$ mol$^{-1}$ cm$^{-1}$ 206300), 514 (14500), 543 (13600), 593 (6600), 645 (24800), $\delta_H$(500 MHz; CDCl$_3$) 8.73-8.71 (m, 2H, β-H), 8.59 (2 s, 2H, β-H), 8.13 (d, J=4.6 Hz, 2H, β-H), 7.81-6.95 (m, 20H, Ar), 5.98-5.87 (m, 2H, Ar), 3.97 (s, 3H, OCH$_3$), 3.95 (s, 3H, OCH$_3$), 3.87 (s, 3H, OCH$_3$), 3.73, 3.71 (2 s, 1H, β-OH), 3.62, 3.60 (2 s, 1H, β-OH), 3.44, 3.42 (2 s, 3H, OCH$_3$), −1.70 (s, 2H, NH); m/z (ESI) 1193.3120 ([M+H]$^+$, $C_{64}H_{45}F_{12}N_4O_6^+$ requires 1193.3142).

4.2 Preparation of 5,10,15,20-tetrakis-(3-hydroxyphenyl)-7,8-bis-[3,5-bis-(trifluoromethyl)-phenyl]-7,8-dihydroxy-7,8-chlorin In a typical experiment, a solution of 5,10,15,20-tetrakis-(3-methoxyphenyl)-7,8-bis-[3,5-bis-(trifluoromethyl)-phenyl]-7,8-dihydroxy-7,8-chlorin (50 mg, 0.04 mmol) in dry dichloromethane (15 ml), under argon atmosphere, was cooled to −60° C. A boron tribromide solution (1 M, 800 µl) in dichloromethane was added dropwise over a period of 10 min. The reaction mixture was allowed to warm up slowly to room temperature and stirred for 18 h. Then, water (20 ml) and ethyl acetate (50 ml) were added as well as sodium hydroxide solution 30% until neutral. The organic layer was separated, washed with water (2×50 ml), dried over anhydrous sodium sulfate and the solvent was removed. The residue was purified by flash chromatography with dichloromethane/methanol 95:5 as eluent. Further purification was achieved by column chromatography with C$_{18}$ reversed phase silica gel using methanol/water 95:5 as eluent. The title compound 5,10,15,20-tetrakis-(3-hydroxyphenyl)-7,8-bis-[3,5-bis-(trifluoromethyl)-phenyl]-7,8-dihydroxy-7,8-chlorin was obtained after recrystallization from dichloromethane/aqueous methanol (27 mg, 57%).

5,10,15,20-Tetrakis-(3-hydroxyphenyl)-7,8-bis-[3,5-bis-(trifluoromethyl)-phenyl]-7,8-dihydroxy-7,8-chlorin

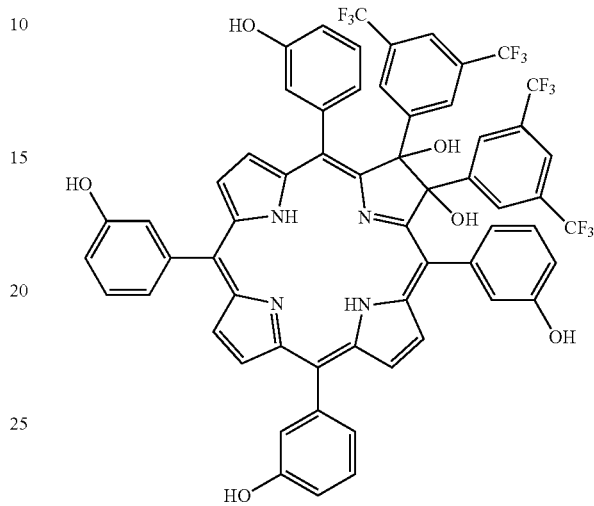

violet solid; mp: 235° C.; $\lambda_{max}$ ((CH$_3$)$_2$CO)/nm 412 ($\epsilon$/dm$^3$ mol$^{-1}$ cm$^{-1}$ 213300), 514 (18300), 543 (17800), 592 (9000), 644 (25000); $\delta_F$ (376 MHz; (CD$_3$)$_2$CO) −63.14, −63.17 (2 s, 6F, 2×CF$_3$), −63.27, −63.28 (2 s, 6F, 2×CF$_3$); m/z (ESI) 1193.3120 ([M+H]$^+$, $C_{64}H_{45}F_{12}N_4O_6^+$ requires 1193.3142).

Example 5

Cell Tests of Selected Compounds in the HT 29 Cell Line

The photosensitizing activity was determined in the human colon adenocarcinoma cell line HT29. The HT29 cell lines were grown in DMEM (cc-pro GmbH) supplemented with 10% heat-inactivated fetal calf serum (FCS, cc-pro GmbH), 1% penicillin (10000 IU) and streptomycin (10000 µg/ml, cc-pro GmbH). Cells were kept as a monolayer culture in a humidified incubator (5% CO$_2$ in air at 37° C.).

A photosensitizer stock solution (2 mM) was performed in DMSO and was kept in the dark at 4° C. Further dilution was performed in RPMI 1640 medium, without phenol red supplemented with 10% FCS to reach a final photosensitizer concentration of 2 or 10 µM, respectively.

2·10$^5$ cells/ml were seeded in micro plates (2·10$^4$ cells/well). Cells were incubated with fresh medium (RPMI without phenol red) containing 10% FCS with 2 or 10 µM of the photosensitizer, for 24 h before light exposure. Before photosensitization, cells were washed, incubated with RPMI without phenol red and 10% FCS, then irradiated at room temperature with a 652 nm diode laser (Ceralas PDT 652, biolitec AG) at a fixed fluence rate of 100 mW/cm$^2$ (50 J/cm$^2$). Following irradiation, cells were incubated in a humidified incubator (5% CO$_2$ in air at 37° C.) for 24 h until cell viability assay.

The cell viability was assessed by the XTT assay. 500 mg XTT (sodium 3'-[phenylaminocarbonyl)-3,4-tetrazolium]-bis(4-methoxy-6-nitro)benzene sulfonic acid, Applichem GmbH) is dissolved in 500 ml PBS-buffer (without Ca$^{2+}$ and Mg²) and sterile filtered. Solution was stored in the dark at −20° C. until use. A sterile solution containing PMS (N-methyl dibenzopyrazine methyl sulfate, Applichem GmbH) was needed as an activation reagent for the XTT. 0.383 mg PMS were dissolved in 1 ml PBS-buffer. The solution should be stored frozen and should not be exposed to light. The XTT reagent solution was thawed in a 37° C. water bath and the activation solution (PMS) was added immediately prior to use. To prepare a reaction solution sufficient for one micro plate (96 wells), 0.1 ml activation solution (PMS) was given to 5 ml XTT reagent. The medium in the micro plate was exchanged with fresh RPMI without phenol red and 10% FCS (100 µl) prior adding 50 µl XTT reaction solution per well. The micro plate was incubated for 2-3 hours at 37° C. and 5% $CO_2$ until an orange dye is to be formed. The micro plate has been shaken gently to evenly distribute the dye in the wells.

The absorbance of the samples was measured with a spectrophotometer (Bio-Kinetics Reader EL312 e; Bio-Tek Instruments Inc.) at a wavelength of 490 nm. In order to measure reference absorbance (to measure non-specific readings) a wavelength of 630-690 nm was used.

Figure 9:
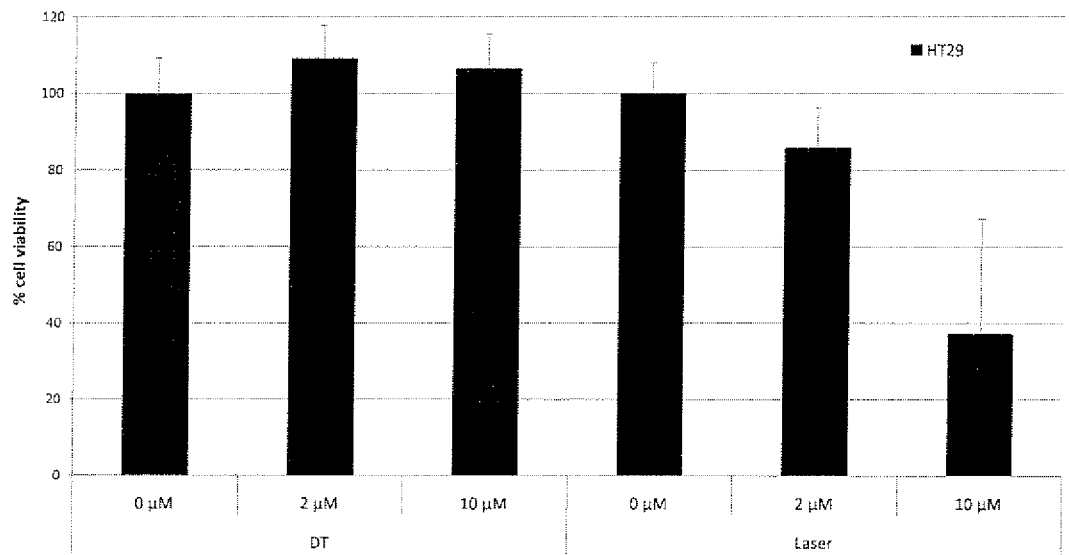
FIG. 9—shows an embodiment of photodynamic activity of 5,10,15,20-tetrakis-(3-hydroxyphenyl)-7,8-bis-(trifluoromethyl)-7,8-dihydroxy-7,8-chlorin against HT29 cell line.
Figure 10:
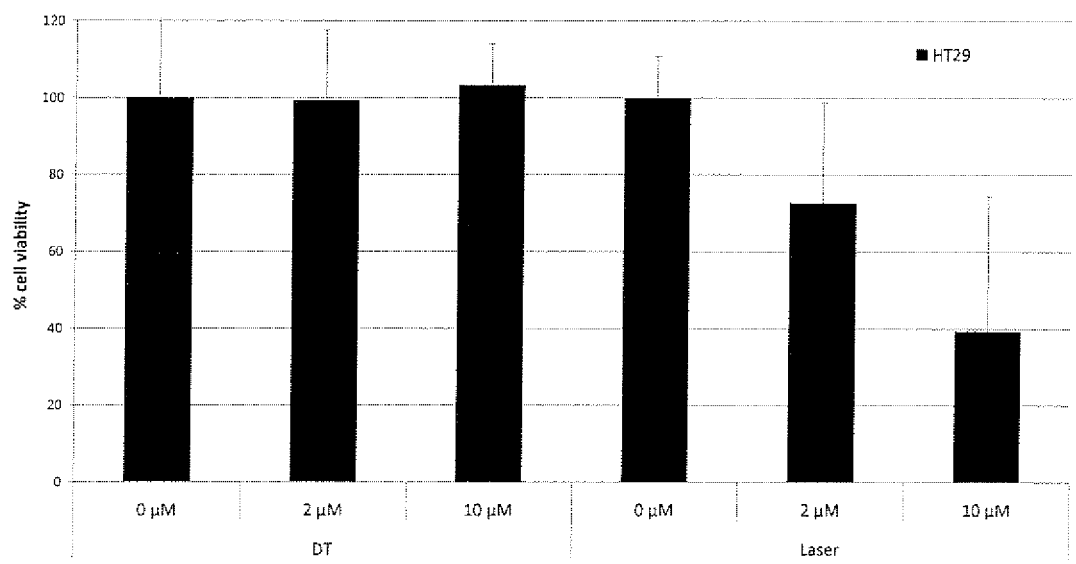
FIG. 10—shows an embodiment of photodynamic activity of 5,10,15,20-tetrakis-(3-hydroxyphenyl)-7,8-dihexyl-7,8-dihydroxy-7,8-chlorin against HT29 cell line.
Figure 11:
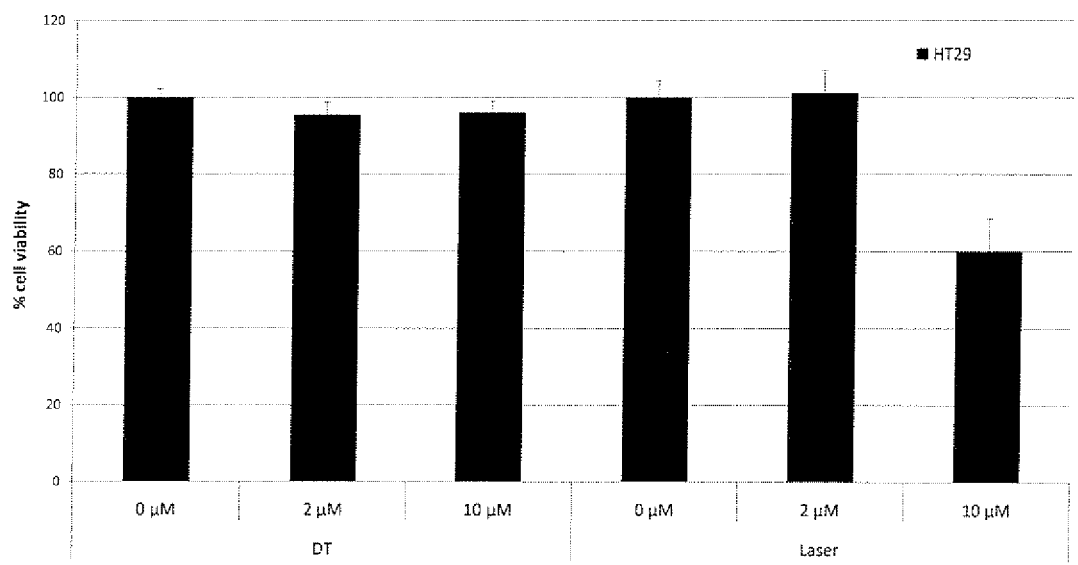
FIG. 11—shows an embodiment of photodynamic activity of 5,10,15,20-tetrakis-(3-hydroxyphenyl)-7,8-bis-[3,5-bis-(trifluoromethyl)-phenyl]-7,8-dihydroxy-7,8-chlorin against HT29 cell line.

FIGS. 9 to 11 illustrate the photodynamic activity (DT means dark toxicity and Laser means phototoxicity) of selected photosensitizers against HT29 cell line, which is known to be very resistant against cell-toxic agents and PDT as well.

Example 6

Cell Tests of Selected Compounds in a Rabbit Synoviocyte and a Mouse Macrophage Cell Line, HIG82 and J1774A.1, Respectively The mouse monocytes-macrophages cell line J774A.1 and the rabbit synoviocyte cell line HIG-82 were grown in DMEM (cc-pro GmbH) supplemented with 10% heat-inactivated fetal calf serum (FCS, cc-pro GmbH), 1% penicillin (10000 IU) and streptomycin (10 000 µg/ml, cc-pro GmbH). Cells were kept as a monolayer culture in a humidified incubator (5% $CO_2$ in air at 37° C.).

A photosensitizer stock solution (2 mM) was performed in DMSO and was kept in the dark at 4° C. Further dilution was performed in RPMI 1640 medium without phenol red supplemented with 10% FCS, to reach a final photosensitizer concentration of 2 or 10 µM, respectively.

$2·10^5$ cells/ml were seeded in micro plates ($2·10^4$ cells/well). Cells were incubated with fresh medium (RPMI without phenol red) containing 10% FCS with 2 or 10 µM of the photosensitizer, for 24 h before light exposure. Before photosensitization, cells were washed, incubated with RPM without phenol red and 10% FCS, then irradiated at room temperature with a 652 nm diode laser (Ceralas PDT 652, biolitec AG) at a fixed fluence rate of 100 mW/cm² (50 J/cm²). Following irradiation, cells were incubated in a humidified incubator (5% $CO_2$ in air at 37° C.) for 24 h until cell viability assay.

The cell viability was assessed by the XTT assay. 500 mg XTT (sodium 3'-[phenylaminocarbonyl)-3,4-tetrazolium]-bis(4-methoxy-6-nitro)benzene sulfonic acid, Applichem GmbH) was dissolved in 500 ml PBS-buffer (without $Ca^{2+}$ and Mg²) and sterile filtered. Solution was stored in the dark at −20° C. until use. A sterile solution containing PMS (N-methyl dibenzopyrazine methyl sulfate, Applichem GmbH) was needed as an activation reagent for the XTT. 0.383 mg PMS were dissolved in 1 ml PBS-buffer. The solution was stored frozen and was not exposed to light. The XTT reagent solution was thawed in a 37° C. water bath and the activation solution (PMS) was added immediately prior to use. To prepare a reaction solution sufficient for one micro plate (96 wells), 0.1 ml activation solution (PMS) was given to 5 ml XTT reagent. The medium in the micro plate was exchanged with fresh RPMI without phenol red and 10% FCS (100 µl), prior adding 50 µl XTT reaction solution per well. The micro plate was incubated for 2-3 hours at 37° C. and 5% $CO_2$ until an orange dye was formed. The micro plate was shaken gently to evenly distribute the dye in the wells.

The absorbance of the samples was measured with a spectrophotometer (Bio-Kinetics Reader EL312 e; Bio-Tek Instruments Inc.) at a wavelength of 490 nm. In order to measure reference absorbance (to measure non-specific readings), a wavelength of 630-690 nm was used.

Figure 12:
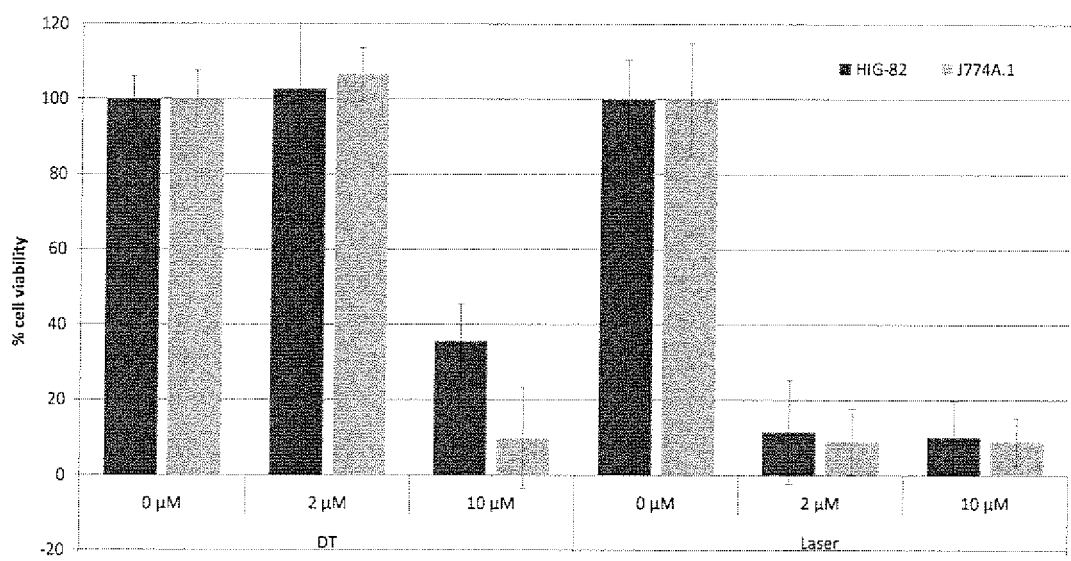
FIG. 12—shows an embodiment of photodynamic activity of 5,10,15,20-tetrakis-(3-hydroxyphenyl)-7,8-bis-(trifluoromethyl)-7,8-dihydroxy-7,8-chlorin against synoviocytes and macrophages.
Figure 13:
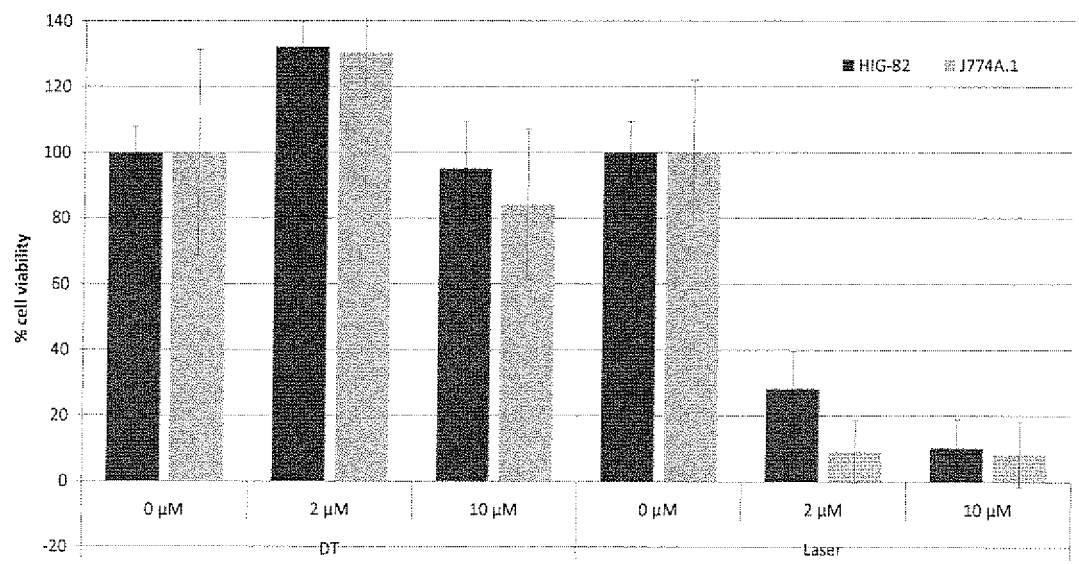
FIG. 13—shows an embodiment of photodynamic activity of 5,10,15,20-tetrakis-(3-hydroxyphenyl)-7,8-dihexyl-7,8-dihydroxy-7,8-chlorin against synoviocytes and macrophages.
Figure 14:
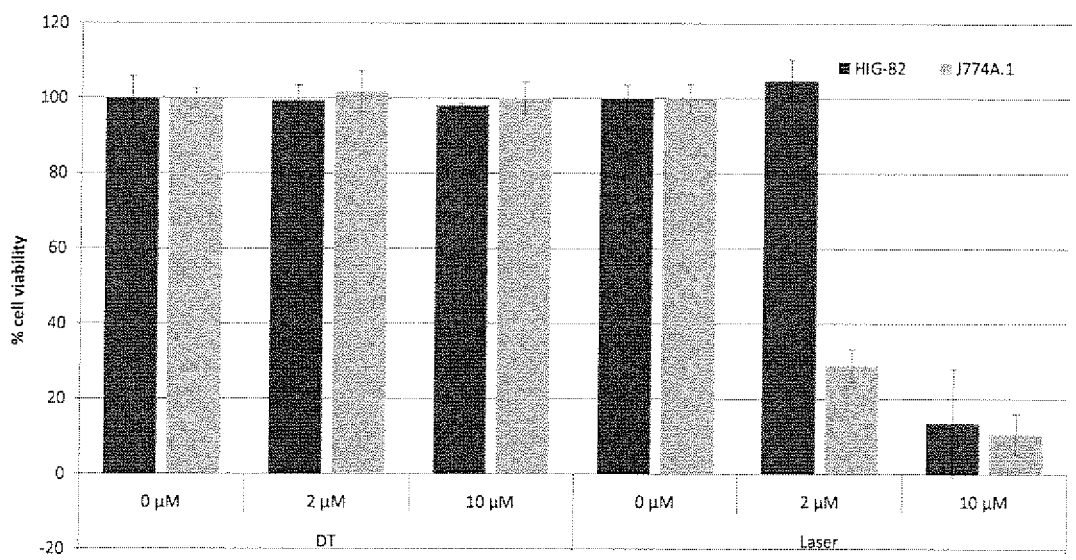
FIG. 14—shows an embodiment of photodynamic activity of 5,10,15,20-tetrakis-(3-hydroxyphenyl)-7,8-bis-[3,5-bis-(trifluoromethyl)-phenyl]-7,8-dihydroxy-7,8-chlorin against synoviocytes and macrophages.

FIGS. 12 to 14 illustrate the photodynamic activity of selected photosensitizers against synoviocytes and macrophages, cell types which are especially relevant for the treatment of arthritis and similar inflammatory diseases.

Having described preferred embodiments of the invention with reference to the accompanying examples, it is to be understood that the invention is not limited to the precise embodiments, and that various changes and modifications may be effected therein by skilled in the art without departing from the scope of the invention as defined in the appended claims.

What is claimed is:

1. A tetrapyrrolic compound comprising formula:

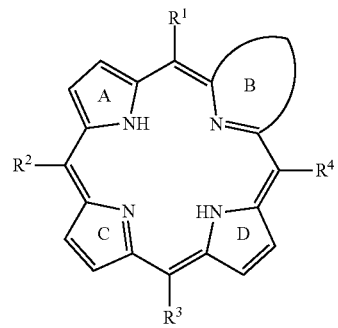

wherein B is selected from the group consisting of:

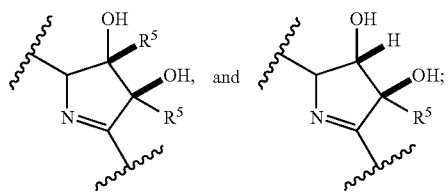

wherein $R^1$, $R^2$, $R^3$ and $R^4$ are independently selected from the group consisting of a hydrogen, an alkyl group or fluoroalkyl group comprising 1-15 carbon atoms, a phenyl ring, and a phenyl ring with one or more substituent X;

wherein R⁵ is selected from the group consisting of an alkenyl comprising 2-15 carbon atoms, an alkynyl comprising 2-15 carbon atoms, a fluoroalkyl group comprising 1-15 carbon atoms, a phenyl ring and a phenyl ring with one or more substituents X;

wherein said one or more substituent X of the phenyl ring is in the ortho-, meta- or para-position;

wherein said one or more substituent X is selected from the group consisting of OCH₃, OH, —COOH, —NH₂, —CF₃, —F, —COOY, —NHY, —OY, —NH—Z—COOH, —CONHCH₂(CH₂)ₙCOOH and —CO—Z—NH₂;

wherein the substituent Y of said substituent X is a polyethylene glycol residue containing a (CH₂CH₂O)ₙ moiety with n=1-30;

wherein the substituent Z of said substituent X is selected from the group consisting of peptides and oligopeptides.

2. The tetrapyrrolic compound according to claim 1, wherein R¹, R², R³ and R⁴ are independently selected from the group consisting of a hydrogen, an alkyl group or fluoroalkyl group comprising 1-15 carbon atoms, a phenyl ring, and a phenyl ring with one or more substituents X;

wherein said one or more substituent X of the phenyl ring is in the ortho-, meta- or para-position;

wherein said one or more substituent X is selected from the group consisting of OCH₃, OH, —COOH, —NH₂, —CF₃, —F, —COOY, —NHY, —OY, —NH—Z—COOH, —CONHCH₂(CH₂)ₙ COOH and —CO—Z—NH₂;

wherein said substituent Y of said substituent X is a polyethylene glycol residue containing a (CH₂CH₂O)ₙ moiety with n=1-30;

wherein said substituent Z of said substituent X is selected from the group consisting of peptides and oligopeptides;

wherein R⁵ is selected from the group consisting of an alkenyl comprising 2-15 carbon atoms, an alkynyl comprising 2-15 carbon atoms, a fluoroalkyl group comprising 1-15 carbon atoms, and a phenyl ring substituted with one or more CF₃-groups;

wherein said one or more CF₃-groups are in the ortho-, meta- or para-position.

3. The tetrapyrrolic compound according to claim 1, wherein R¹, R², R³ and R⁴ are independently selected from the group consisting of an alkyl or fluoroalkyl group comprising 4-15 carbon atoms, and a phenyl ring with one or more substituents X;

wherein said one or more substituent X is in the ortho-, meta- or para-position;

wherein said one or more substituent X is selected from the group consisting of OCH₃, OH, —COOH, —NH₂;

wherein R⁵ is selected from the group consisting of an alkenyl comprising 2-15 carbon atoms, an alkynyl comprising 2-15 carbon atoms, a fluoroalkyl group comprising 1-15 carbon atoms, and a phenyl ring substituted with one or more CF₃-groups;

wherein said one or more CF₃-groups are in the ortho-, meta- or para-position.

4. The tetrapyrrolic compound according to claim 1, comprising formula:

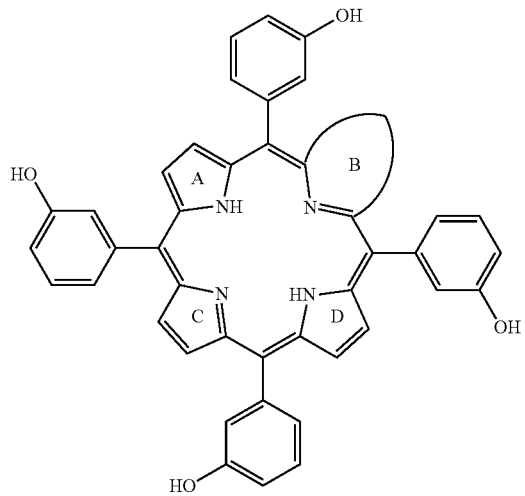

wherein B is

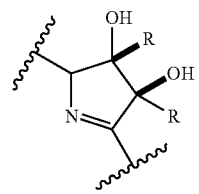

wherein R is selected from the group consisting of an alkenyl comprising 2-15 carbon atoms, an alkynyl comprising 2-15 carbon atoms, a fluoroalkyl group comprising 1-15 carbon atoms, a phenyl ring, and a phenyl ring with one or more substituents X;

wherein said one or more substituent X is in the ortho-, meta- or para-position; wherein said one or more substituent X is selected from the group consisting of OCH₃, OH, —COOH, —NH₂, —CF₃, —F, —COOY, —NHY, —OY, —NH—Z—COOH, —CONHCH₂(CH₂)ₙ COOH and —CO—Z—NH₂;

wherein the substituent Y of said substituent X is selected from the group consisting of a polyethylene glycol residue containing a (CH₂CH₂O)ₙ moiety with n=1-30;

wherein the substituent Z of said substituent X is selected from the group consisting of peptides and oligopeptides.

5. The tetrapyrrolic compound according to claim 4, wherein R is selected from the group consisting of an alkenyl comprising 2-15 carbon atoms, an alkynyl comprising 2-15 carbon atoms, a fluoroalkyl group comprising 1-15 carbon atoms, and a phenyl ring substituted with one or more CF₃-groups; wherein said one or more CF₃-groups are in the ortho-, meta- or para-position.

6. The tetrapyrrolic compound according to claim 1, comprising formula:

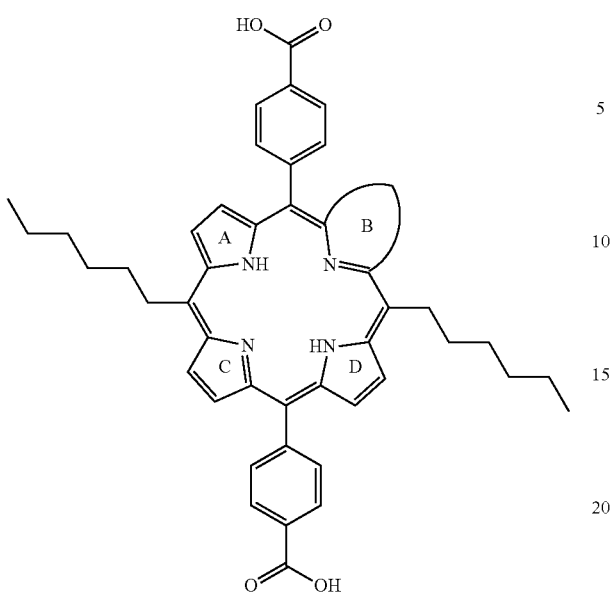

wherein B is

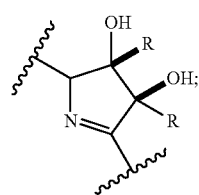

wherein R is selected from the group consisting of an alkenyl comprising 2-15 carbon atoms, an alkynyl comprising 2-15 carbon atoms, a fluoroalkyl group comprising 1-15 carbon atoms, a phenyl ring, and a phenyl ring with one or more substituents X;
wherein said one or more substituent X is in the ortho-, meta- or para-position;
wherein said one or more substituent X is selected from the group consisting of $OCH_3$, OH, —COOH, —$NH_2$, —$CF_3$, —F, —COOY, —NHY, —OY, —NH—Z—COOH, —CONH$CH_2$($CH_2$)$_n$ COOH and —CO—Z—$NH_2$;
wherein the substituent Y of said substituent X is selected from the group consisting of a polyethylene glycol residue containing a ($CH_2CH_2O$)$_n$ moiety with n=1-30;
wherein the substituent Z of said substituent X is selected from the group consisting of peptides and oligopeptides.

7. The tetrapyrrolic compound according to claim 6, wherein R is selected from the group consisting of an alkenyl comprising 2-15 carbon atoms, an alkynyl comprising 2-15 carbon atoms, a fluoroalkyl group comprising 1-15 carbon atoms, and a phenyl ring substituted with one or more $CF_3$-groups; wherein said one or more $CF_3$-groups are in the ortho-, meta- or para-position.

8. The tetrapyrrolic compound according to claim 1, comprising formula:

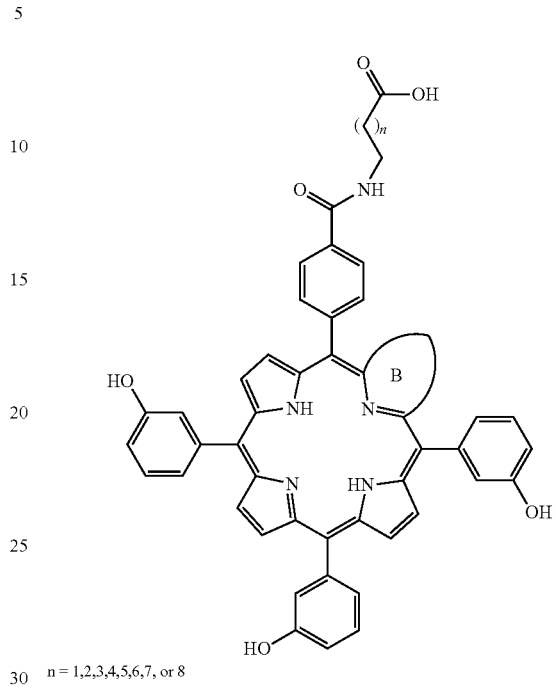

n = 1,2,3,4,5,6,7, or 8 wherein B is

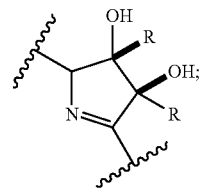

wherein R is selected from the group consisting of an alkenyl comprising 2-15 carbon atoms, alkynyl comprising 2-15 carbon atoms, a fluoroalkyl group comprising 1-15 carbon atoms, a phenyl ring, and a phenyl ring with one or more substituents X;
wherein said one or more substituent X is in the ortho-, meta- or para-position;
wherein said one or more substituent X is selected from the group consisting of $OCH_3$, OH, —COOH, —$NH_2$, —$CF_3$, —F, —COOY, —NHY, —OY, —NH—Z—COOH, —CONH$CH_2$($CH_2$)$_n$COOH and —CO—Z—$NH_2$;
wherein the substituent Y of said substituent X is selected from the group consisting of a polyethylene glycol residue containing a ($CH_2CH_2O$)$_n$ moiety with n=1-30;
wherein the substituent Z of said substituent X is selected from the group consisting of peptides and oligopeptides.

9. The tetrapyrrolic compound according to claim 8, wherein R is selected from the group consisting of an alkenyl comprising 2-15 carbon atoms, a fluoroalkyl group comprising 1-15 carbon atoms, and a phenyl ring substituted with one or more $CF_3$-groups; wherein said one or more $CF_3$-groups are in the ortho-, meta- or para-position.

10. The tetrapyrrolic compound according to claim 1, comprising formula:

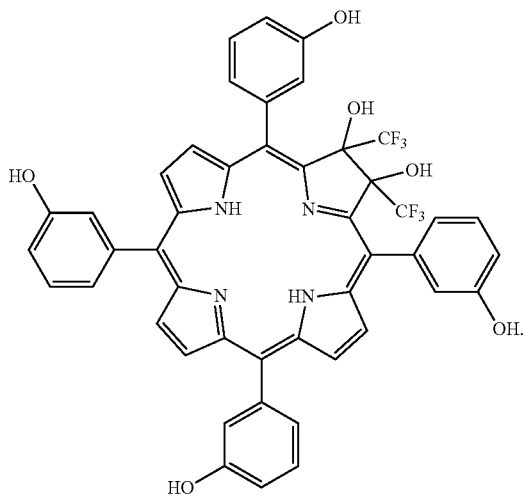 [SMILES: Oc1cccc(-c2c3nc(c(-c4cccc(O)c4)c4ccc([nH]4)c(-c4cccc(O)c4)c4nc(c(-c5cccc(O)c5)c5ccc2[nH]5)C(O)(C(F)(F)F)C4(O)C(F)(F)F)C=C3)c1]

11. The tetrapyrrolic compound according to claim 1, comprising formula:

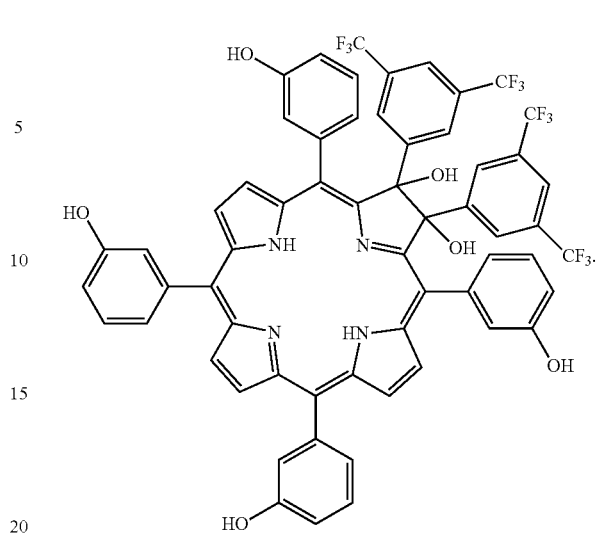

12. A pharmaceutical composition comprising a compound according to claim 1 as an active ingredient.

13. The pharmaceutical composition according to claim 12, wherein said pharmaceutical composition is a liposomal formulation.

14. The pharmaceutical composition according to claim 12, wherein said active ingredient is formulated in carriers selected from the group consisting of conventional liposomes, pegylated liposomes, nanoemulsions, nanocrystrals, nanoparticles, fatty emulsions, lipidic formulations, self-micro-emulsifying-drug-delivery-systems, Alpha-Feto protein (AFP), Bovine-Serum-Albumin (BSA), poly(lactic-co-glycolic acid) (PLGA), fatty emulsions, organic nanoparticles, and non-organic nanoparticles.

* * * * *